US011793572B2

United States Patent
Wang et al.

(10) Patent No.: US 11,793,572 B2
(45) Date of Patent: *Oct. 24, 2023

(54) SELECTING A MEDICAL DEVICE FOR USE IN A MEDICAL PROCEDURE

(71) Applicant: Henry Ford Health System, Detroit, MI (US)

(72) Inventors: Dee Dee Wang, Ann Arbor, MI (US); Michael Forbes, Dearborn, MI (US); Eric Myers, Ferndale, MI (US); William O'Neill, Grosse Pointe Farms, MI (US)

(73) Assignee: HENRY FORD HEALTH SYSTEM, Detroit, MI (US)

( * ) Notice: Subject to any disclaimer, the term of this patent is extended or adjusted under 35 U.S.C. 154(b) by 28 days.

This patent is subject to a terminal disclaimer.

(21) Appl. No.: 17/012,138

(22) Filed: Sep. 4, 2020

(65) Prior Publication Data

US 2021/0093383 A1    Apr. 1, 2021

Related U.S. Application Data

(63) Continuation of application No. 15/806,819, filed on Nov. 8, 2017, now Pat. No. 10,792,104.

(Continued)

(51) Int. Cl.
*A61B 34/10*    (2016.01)
*A61B 17/12*    (2006.01)
(Continued)

(52) U.S. Cl.
CPC ........ *A61B 34/10* (2016.02); *A61B 17/12031* (2013.01); *A61B 17/12122* (2013.01);
(Continued)

(58) Field of Classification Search
CPC ................ A61B 34/10; A61B 2576/00; A61B 17/12031; A61B 17/12122;
(Continued)

(56) References Cited

U.S. PATENT DOCUMENTS 7,371,067 B2    5/2008    Anderson et al.
8,494,245 B2    7/2013    Liao et al.
(Continued)

FOREIGN PATENT DOCUMENTS

EP    1749493 A1    2/2007
JP    5964862 B2    8/2016
(Continued)

OTHER PUBLICATIONS

Amar Krishnaswamy et al., "Planning left atrial appendage occlusion using cardiac multidetector computed tomography", May 21, 2012, Letters to the Editor, pp. 313-317 (Year: 2012).*

(Continued)

*Primary Examiner* — Patricia J Park
*Assistant Examiner* — Adil Partap S Virk
(74) *Attorney, Agent, or Firm* — REISING ETHINGTON, P.C.

(57) ABSTRACT

A method for selecting a medical device for use in the performance of a medical procedure. The method comprises acquiring image data relating to an anatomical region of interest of a patient's body and generating a multi-dimensional depiction of the anatomical region of interest using the acquired image data. The method further comprises defining a plurality of points relative to the multi-dimensional depiction, determining one or more measurements based on the defined plurality of points, and then selecting a medical device to be used based on the determined measurements.

15 Claims, 18 Drawing Sheets

Related U.S. Application Data

(60) Provisional application No. 62/419,072, filed on Nov. 8, 2016.

(51) Int. Cl.
    *A61B 34/00* (2016.01)
    *A61B 90/00* (2016.01)
    *A61B 17/00* (2006.01)

(52) U.S. Cl.
    CPC ............... *A61B 2017/00243* (2013.01); *A61B 2017/00292* (2013.01); *A61B 2017/00632* (2013.01); *A61B 2017/1205* (2013.01); *A61B 2034/105* (2016.02); *A61B 2034/107* (2016.02); *A61B 2034/108* (2016.02); *A61B 2034/256* (2016.02); *A61B 2090/374* (2016.02); *A61B 2090/378* (2016.02); *A61B 2090/3762* (2016.02); *A61B 2576/00* (2013.01)

(58) Field of Classification Search
    CPC ........... A61B 2017/00243; A61B 2017/00292; A61B 2017/00632; A61B 2017/1205; A61B 2034/105; A61B 2034/107; A61B 2034/108; A61B 2034/256; A61B 2090/374; A61B 2090/3762; A61B 2090/378
    See application file for complete search history.

(56) References Cited

U.S. PATENT DOCUMENTS

| | | | |
|---|---|---|---|
| 8,666,714 | B2 | 3/2014 | Whirley et al. |
| 8,771,189 | B2* | 7/2014 | Ionasec .................. G06T 7/262 600/437 |
| 8,775,133 | B2 | 7/2014 | Schroeder |
| 8,830,233 | B2 | 9/2014 | Friedland et al. |
| 9,693,830 | B2 | 7/2017 | Wang et al. |
| 9,875,339 | B2 | 1/2018 | Yelin et al. |
| 10,792,104 | B2* | 10/2020 | Wang ..................... A61B 34/10 |
| 2003/0023266 | A1 | 1/2003 | Borillo et al. |
| 2004/0186566 | A1* | 9/2004 | Hindrichs ............. A61F 2/2487 623/2.37 |
| 2007/0293734 | A1 | 12/2007 | Coste-Maniere et al. |
| 2010/0240996 | A1 | 9/2010 | Ionasec et al. |
| 2011/0077507 | A1 | 3/2011 | Krishnan |
| 2011/0153286 | A1* | 6/2011 | Zaeuner .................. G06T 17/00 703/1 |
| 2012/0232386 | A1 | 9/2012 | Mansi et al. |
| 2012/0323545 | A1 | 12/2012 | Aulbach et al. |
| 2013/0073025 | A1 | 3/2013 | Kassab |
| 2013/0129173 | A1 | 5/2013 | Grbic et al. |
| 2013/0230225 | A1 | 9/2013 | Waechter-Stehle et al. |
| 2014/0088698 | A1 | 3/2014 | Roels et al. |
| 2015/0104085 | A1 | 4/2015 | Schilling et al. |
| 2015/0112427 | A1 | 4/2015 | Schweich, Jr. et al. |
| 2015/0119692 | A1 | 4/2015 | McHenry et al. |
| 2016/0038246 | A1 | 2/2016 | Wang et al. |
| 2016/0166332 | A1 | 6/2016 | Wang et al. |
| 2017/0084029 | A1* | 3/2017 | Piazza ..................... G06T 17/10 |
| 2019/0021699 | A1 | 1/2019 | Bracken et al. |

FOREIGN PATENT DOCUMENTS

| | | |
|---|---|---|
| WO | WO03007825 A1 | 1/2003 |
| WO | WO2013171039 A1 | 11/2013 |
| WO | WO2015179543 A1 | 11/2015 |

OTHER PUBLICATIONS

Doyle et al., "Vessel asymmetry as an additional diagnostic tool in the assessment of abdominal aortic aneurysms", Feb. 2009, Society of Vascular Surgery, pp. 443-454 (Year: 2009).*

Moyer et al., "Wall-Motion Based Analysis of Global and Regional Left Atrial Mechanics", Oct. 2013, IEEE Transactions on Medical Imaging, vol. 32, No. 10. pp. 1765-1776 (Year: 2013).*

Jungen et al. "Left Atrial Appendage Closure Guided by Integrated Echocardiography and Fluoroscopy Imaging Reduces Radiation Exposure", Oct. 14, 2015, PLOS ONE, pp. 1-13 (Year: 2015).*

Ionasec et al., "Patient-Specific Modeling and Quantification of the Aortic and Mitral Valves From 4-D Cardiac CT and TEE", May 3, 2010, IEEE Transactions on Medical Imaging, vol. 29, No. 9, pp. 1636-1651 (Year: 2010).*

Materialise (Mimics SE Mimics Student Edition Course Book, 2016) (Year: 2016).*

Moyer et al., "Wall-Motion Based Analysis of Global and Regional Left Atrial Mechanics", Oct. 2013, IEEE Transactions on Medical Imaging, vol. 32, No. 10 (Year: 2013).*

Maslow, Andrew D., et al.; Echocardiographic Predictors of Left Ventricular Outflow Tract Obstruction and Systolic Anterior Motion of the Mitral Valve after Mitral Valve Reconstruction for Myxomatous Valve Disease; Journal of the American College of Cardiology; Aug. 30, 1999, 9 pages, vol. 34, No. 7; Published by Elsevier Science Inc.

Lang; Roberto M., et al.; Recommendations for Chamber Quantification; The European Society of Cardiology; Dec. 23, 2005, 30 pages; Published by Elsevier Ltd.

Tops; Laurens F., et al.; Noninvasive Evaluation of the Aortic Root with Multislice Computed Tomography, Implications for Transcatheter Aortic Valve Replacement; Journal of the American College of Cardiology; Dec. 16, 2007, 10 pages, vol. 1, No. 3; Published by Elsevier Science Inc.

Gijsen; Frank JH, et al.; Simulation of Stent Deployment in a Realistic Human Coronary Artery; Aug. 6, 2008, 11 pages; Published by BioMedical Engineering OnLine.

Schoenhagen; Paul, et al.; Three-Dimensional Imaging of the Aortic Valve and Aortic Root with Computed Tomography: New Standards in an Era of Transcatheter Valve Repair/Implantation; European Heart Journal; May 13, 2009, 8 pages; Published by the European Society of Cardiology.

Kurra; Vikram, et al.; Pre-Procedural Imaging of Aortic Root Orientation and Dimensions, Comparison Between X-Ray Angiographic Planar Imaging and 3-Dimensional Multidetector Row Computed Technology; The American College of Cardiology Foundation; Oct. 15, 2009, 9 pages, vol. 3, No. 1; Published by Elsevier Science Inc.

Schoenhagen; Paul, et al.; Three-Dimensional Imaging in the Context of Minimally Invasive and Transcatheter Cardiovascular Interventions using Multi-Detector Computed Tomography: From Pre-Operative Planning to Intra-Operative Guidance; European Heart Journal; Aug. 3, 2010, 15 pages; Published by the European Society of Cardiology.

Quaini; Annalisa, et al.; A Three-Dimensional Computational Fluid Dynamics Model of Regurgitant Mitral Valve Flow: Validation Against In Vitro Standards and 3D Color Doppler Methods; Cardivascular Engineering and Technology; Feb. 8, 2011, 13 pages.

Mihalef; Viorel, et al.; Patient Specific Modelling of Whole Heart Anatomy, Dynamics and Haemodynamics from Four-Dimensional Cardia CT Images; Interface Focus; Mar. 23, 2011, 12 pages.

Jelnin; Vladimir, et al.; Clinical Experience with Percutaneous Left Ventricular Transapical Access for Interventions in Structural Heart Defects, A Safe Access and Secure Exit; The American College of Cardiology Foundation; May 31, 2011, 7 pages, vol. 4, No. 8; Published by Elsevier Inc.

Jabbour; Andrew, et al.; Multimodality Imaging in Transcatheter Aortic Valve Implantation and Post-Procedural Aortic Regurgitation, Comparison Among Magnetic Resonance Cardiac Computed Tomography, and Echocardiography; The American College of Cardiology Foundation; Sep. 13, 2011, 9 pages, vol. 58, No. 21; Published by Elsevier Inc.

Rishnaswamy; Amar, et al.; Planning Left Atrial Appendage Occlusion using Cardiac Multidetector Computed Tomography; International Journal of Cardiology; Year 2012, vol. 158, Issue 2., pp. 313-317.

Schievano; Silvia, et al.; Finite Element Analysis to Study Percutaneous Heart Valves; UCL Institute of Cardiovascular Science; Mar. 30, 2012, 27 pages; Published by InTech.

(56) References Cited

OTHER PUBLICATIONS

Achenbach, Stephan, et al.; SCCT Expert Consensus Document on Computed Tomography Imaging Before Transcatheter Aortic Valve Implantation (TAVI)/Transcatheter Aortic Valve Replacement (TAVR); Journal of Cardiovascular Computed Tomography; Nov. 6, 2012, 15 pages.
Borazjani; Iman, et al.; Left Ventricular Flow Analysis: Recent Advances in Numerical Methods and Applications in Cardiac Ultrasound; Mar. 19, 2013, 12 pages; Hindawi Publishing Corporation.
Litmanovich; Diana E., et al.; Imaging in Transcatheter Aortic Valve Replacement (TAVR): Role of the Radiologist; Insights Imaging; Jan. 21, 2014, 23 pages.
Fast App: Looking Deep into Heart Valve Replacement; http://www.deskeng.com/de/fast-app-looking-deep-into-heart-valve-replacement; Feb. 12, 2014, 4 pages, accessed Oct. 31, 2014.
Guerrero; Mayra, et al.; First in Human Percutaneous Implantation of a Balloon Expandable Transcatheter Heart Valve in a Severly Stenosed Native Mitral Valve; Feb. 15, 2014, 5 pages.
Griffith; Boyce E.; Multi-Beat Simulations of the Fluid Dynamics of the Aortic Heart Valve with Physiological Driving and Loading Conditions using the Immersed Boundary Method; http://www.cims.nyu.edu/~griffith; Jul. 4, 2014, 14 pages, accessed Oct. 31, 2014.
McQueen; David M., et al.; Heart Animations Computed by the Immersed Boundary Method; http://www.math.nyu.edu/faculty/peskin/myo3D/index.html; Copyright 2005, 2 pages, accessed Oct. 31, 2014.
University of California, Health Sciences; Doctors use 3D Printed Model to Guide Tricky Heart Valve Replacement; ScienceDaily; Jul. 1, 2015, 3 pages.
Written Opinion & International Search Report for PCT/US2017/060592 dated Mar. 26, 2018, 13 pages.
Preliminary Report on Patentability for PCT/US2017/060592 dated May 23, 2019, 10 pages.
EP Extended Search Report for EP Application No. 17868612.7 dated May 15, 2020, 13 pages.
CN Office Action for CN Application No. 201780068862.X dated Nov. 3, 2021, 17 pages.
JP Office Action for JP Application No. 2019-523790 dated Aug. 31, 2021, 3 pages.
Chak-Yu So et. al.; Additive Value of Preprocedural Computed Tomography Planning Versus Stand-Alone Transesophageal Echocardiogram Guidance to Left Atrial Appendage Occlusion: Comparison of Real-World Practice; Journal of the American Heart Association; J Am Heart Assoc. 2021;10:e020615. DOI: 10.1161/JAHA.120.020615.
Jasneet Devgun et al.; Pre-cath Laboratory; Planning for Left Atria Appendage Occlusion—Optional or Essential? Intervent Cardiol Clin 11 (2022) 143-152; 2211-7458/22-2021 Elsevier Inc.
Australian Office Action corresponding to Australian Application No. 201735901, dated Jun. 24, 2022, 3 pages.
Office Action issued by the European Patent Office for application 17868612.7 dated Mar. 21, 2023.
Office Action issued by the Japanese Patent Office for application 2022-014847 dated Feb. 7, 2023, includes brief English language summary.

* cited by examiner

SELECTING A MEDICAL DEVICE FOR USE IN A MEDICAL PROCEDURE

CROSS REFERENCE TO RELATED APPLICATIONS

This application is a continuation of U.S. patent application Ser. No. 15/806,819 filed on Nov. 8, 2017, claims the benefit of U.S. Provisional Application No. 62/419,072 filed Nov. 8, 2016. Each of the aforementioned applications are hereby incorporated herein by reference in their entireties.

TECHNICAL FIELD

This disclosure relates generally to periprocedural planning for medical procedures, and more particularly, to periprocedural planning for non-invasive medical procedures involving the heart, including the selection of medical devices to be used in such procedures.

BACKGROUND

Non-invasive percutaneous implantation of cardiac devices poses certain challenges to physicians. As opposed to surgically invasive procedures, such as, for example, open heart surgery, physicians performing non-invasive cardiac implantation procedures have a limited field of view and are generally limited to guidance during the procedure using images generated by two-dimensional (2D) imaging modalities (e.g., ultrasound, fluoroscopy, etc.). Because physicians are typically limited to 2D imaging during the performance of a procedure, proper periprocedural planning and evaluation is required to accurately assess and determine, for example, the size of certain anatomical structures and the type(s) and/or size(s) of devices to be used during the procedure (e.g., catheters).

As with in-procedure guidance, however, conventional periprocedural planning technology has generally been based on imaging platforms and modalities that employ 2D imaging. Accordingly, like the implantation procedure itself, periprocedural planning for such procedures poses challenges to physicians due to the inherent limitations of the conventional 2D imaging that is used.

Accordingly, there is a need for a periprocedural planning method and system that minimizes and/or eliminates one or more of the above-identified deficiencies in conventional periprocedural planning methodologies/techniques.

SUMMARY

According to one embodiment, a method for selecting a medical device for use in the performance of a medical procedure is provided. The method comprises acquiring image data relating to an anatomical region of interest of a patient's body, generating a multi-dimensional depiction of the anatomical region of interest using the acquired image data, defining a plurality of points relative to the multi-dimensional depiction, determining one or more measurements based on the defined plurality of points, and selecting a medical device to be used based on the determined measurements.

According to another embodiment, a non-transitory, computer-readable storage medium storing instructions thereon is provided. The stored instructions are such that when they are executed by one or more electronic processors, the one or more processors are caused to carry out the method of: acquiring image data relating to an anatomical region of interest of a patient's body; generating a multi-dimensional depiction of the anatomical region of interest using the acquired image data; defining a plurality of points relative to the multi-dimensional depiction; determining one or more measurements based on the defined plurality of points; and selecting a medical device to be used based on the determined measurements.

According to yet another embodiment, a system for selecting a medical device of use in a medical procedure is provided. The system comprises an electronic processor and an electronic memory device electrically coupled to the electronic processor and having instructions stored therein. The processor is configured to access the memory device and execute the instructions stored therein such that it is operable to acquire image data relating to an anatomical region of interest of a patient's body, generate a multi-dimensional depiction of the anatomical region of interest using the acquired image data, define a plurality of points relative to the multi-dimensional depiction, determine one or more measurements based on the defined plurality of points, and select a medical device to be used based on the determined measurements.

BRIEF DESCRIPTION OF DRAWINGS

One or more embodiments of the invention will hereinafter be described in conjunction with the appended drawings, wherein like designations denote like elements, and wherein.

DETAILED DESCRIPTION

The system and method described herein can assist physicians in pre-operational planning (also referred to as "periprocedural planning") of percutaneous procedures, for example and without limitation, procedures involving the implantation of medical devices such as prosthetic heart valves, left atrial appendage (LAA) occlusion devices, and the like. Generally, the system and method described herein use advanced imaging and modeling strategies to accurately assess the location and size of various anatomical structures of interest and to determine or select an ideal or optimal type and size of medical device (e.g., catheter) to be used in the performance of a medical procedure (e.g., implantation procedure) that is specific to the particular patient on which the procedure is to be performed. Although the system and method may be applicable to planning for and evaluating a variety of procedures, of particular applicability are procedures involving the LAA, and in particular the implantation of device for occluding the LAA. Accordingly, the description below will be primarily with respect to the selection of a medical device in the form of catheter that is used to deliver an occlusion device to the LAA. It will be appreciated, however, that various teachings set forth herein could also be applied to any number of other procedures, both cardiac-related and otherwise. For example, the teachings may be applied to the selection a catheter for delivering a prosthetic mitral valve to the mitral annulus of the patient's heart. Thus, it will be appreciated that the present disclosure is not intended to be limited to the use of the system and method described herein for any particular type of procedure.

Figure 1:
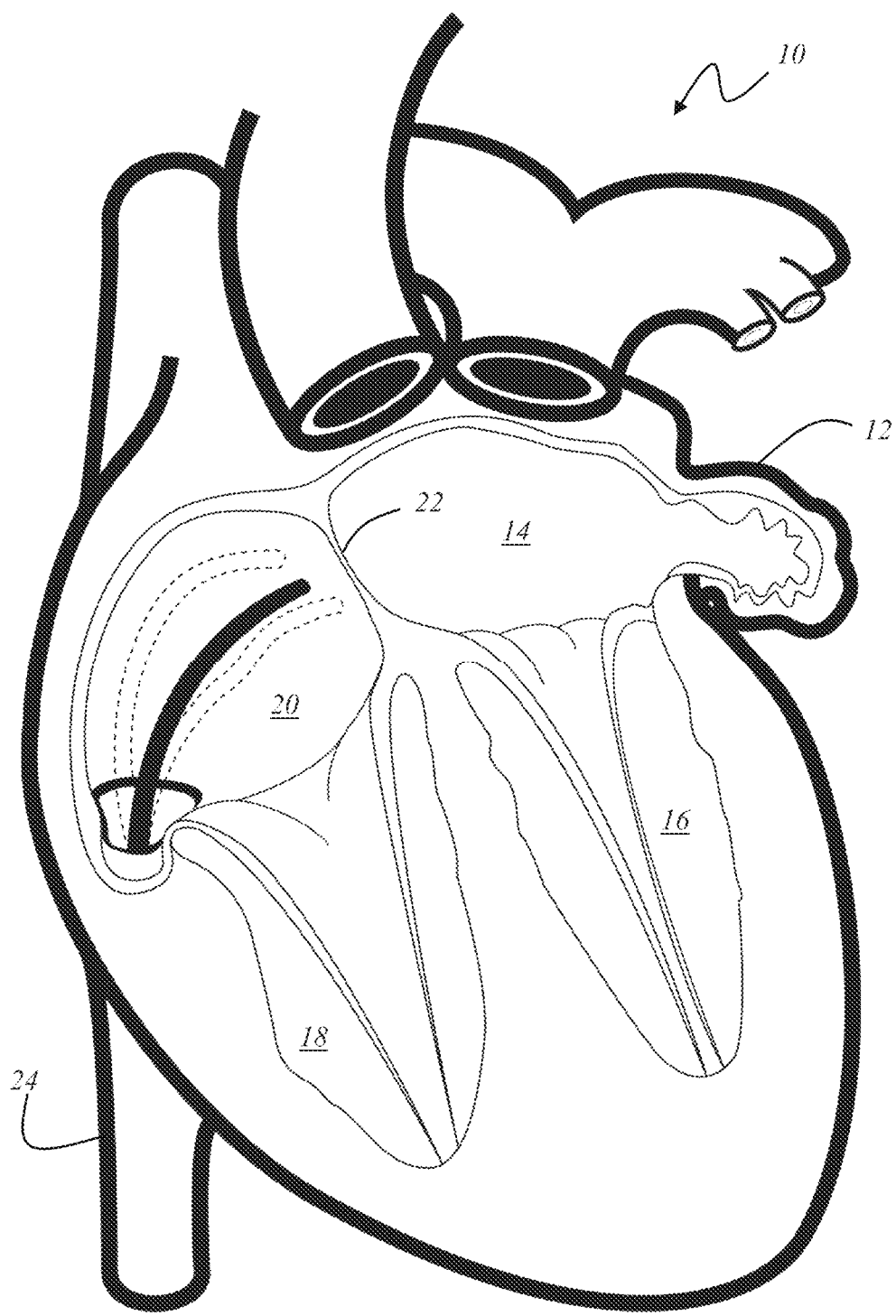
FIG. 1 is a schematic and diagrammatic view a portion of the human heart.

For purposes of context, FIG. 1 illustrates a portion of a human heart 10 including the LAA 12, the left atrium 14, the left ventricle 16, the right ventricle 18, the right atrium 20, the interatrial wall 22, and the inferior vena cava (IVC) 24. The LAA is a pocket of sorts that receives blood from, and drains blood into, the left atrium. Although the LAA does not contribute to or serve an important function in the operation of the heart, it is a site of concern as it relates to cardiac thrombosis. More specifically, the LAA provides an area within the heart where blood may collect or pool, coagulate, and form a clot. It is well known that blood clots and other emboli traveling through the bloodstream of a patient can have deleterious effects. A clot in the LAA may migrate from the LAA into the left atrium, pass through the mitral valve into the left ventricle, travel through the aortic valve into the aorta and enter the patient's bloodstream where it may obstruct blood flow to, for example, the heart, lungs, or brain, potentially causing heart attacks, strokes, or other undesirable occurrences.

To mitigate against the migration of clots from the LAA, procedures can be performed to occlude the LAA. For example, an occlusion device, such as, for example, the Watchman® device commercially available from Boston Scientific may be placed and secured at or near the ostium of the LAA. As is known in the art, a special elongate medical device (e.g., a catheter) may be used to deliver such an occlusion device to the appropriate location. In at least one embodiment of the system and methodology described herein, the system and method can be used to, for example, determine or select an ideal or optimal type and size of the catheter that is used in the delivery of the occlusion device to the LAA.

Figure 2:
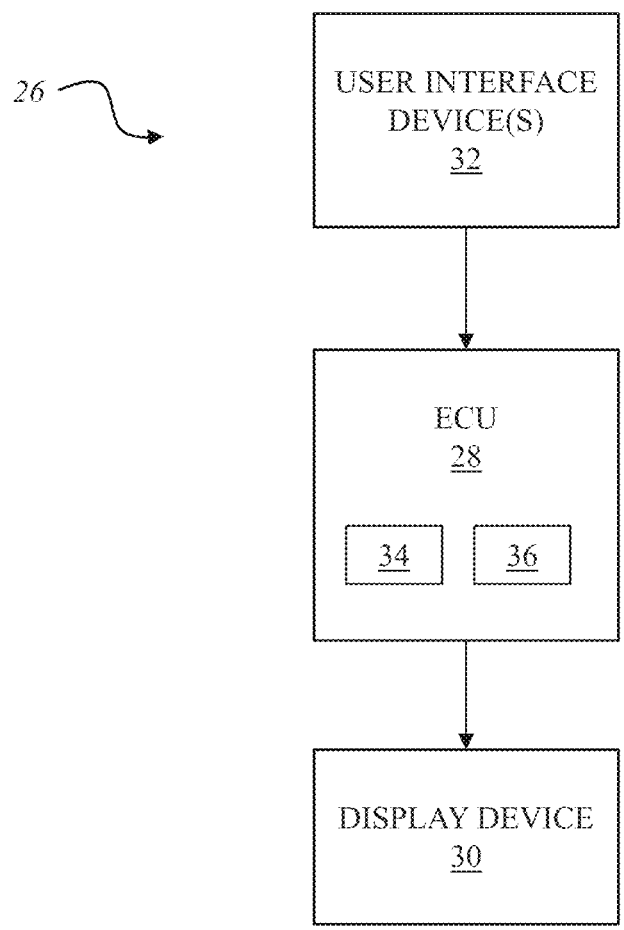
FIG. 2 is a schematic and block diagram of an illustrative embodiment of a system for performing one or more embodiments of the methodology described herein.

FIG. 2 depicts an illustrative embodiment of a system 26 for determining or selecting a medical device to be used in the delivery of a medical device to an anatomical region of interest of a patient's body. In an embodiment, the medical device may comprise an implantable device such as a prosthetic heart valve (e.g. a prosthetic mitral valve) or an occlusion device (e.g., an LAA occlusion device), and the anatomical region of interest is at least a region of the patient's heart. In the illustrative embodiment, the system 26 comprises, among potentially other components, an electronic control unit (ECU) 28, a display device 30, and one or more user interface devices 32.

The ECU 28 may comprise one or more electronic processors 34 having one or more electrical inputs and one or more electrical outputs. The electronic processor 34 may comprise any suitable electronic processor known in the art (e.g., a microprocessor, a microcontroller, an ASIC, etc.) that is configured to execute electronic instructions.

The ECU 28 may further include, or be electrically connected to and/or configured to access, an electronic memory device 36. The memory device 36 may be part of or electrically connected to and/or accessible by the processor 34. The electronic memory device 36 may comprise any suitable memory device known in the art and may store a variety of data, information, and/or instructions therein or thereon. In an embodiment, the memory device 36 has information and instructions for one or more of software, firmware, programs, algorithms, scripts, applications, data structures (e.g., look-up tables) etc. stored therein or thereon that may govern and/or facilitate all or part of the methodology described herein. In at least some embodiments, the memory device 36 may comprise a computer-readable storage medium (e.g. a non-transitory or non-transient storage medium) that may comprise any mechanism for storing information in a form readable by a machine or electronic processors/computational devices (e.g., processor 34), including, without limitation: a magnetic storage medium (e.g. floppy diskette); optical storage medium (e.g. CD-ROM); magneto optical storage medium; read only memory (ROM); random access memory (RAM); erasable programmable memory (e.g. EPROM ad EEPROM); flash memory; or electrical or other types of medium for storing such information/instructions. In addition, program instructions may be communicated using optical, acoustical, or other form of propagated signal (e.g., carrier waves, infrared signals, digital signals, or other types of signals or mediums).

In any event, in an embodiment, the processor 34 may access the memory device 36 and execute and/or use that or those instructions and information to carry out or perform some or all of the functionality and methodology describe herein.

The display device 30 may comprise any number of display devices known in the art, for example and without limitation, liquid crystal display (LCD), cathode ray tube (CRT), plasma, or light emitting diode (LED) monitors or displays. The display device 30 is electrically connected to coupled to the ECU 28 and is configured to be controlled by the ECU 28 such that images, models, or depictions of, for example, anatomical structures generated, obtained, or acquired by the ECU 28—including those used in performing the method described below—may be displayed thereon and may be used for the purposes described herein. Additionally, in an embodiment wherein the ECU 28 may be configured to generate an interactive graphical user interface (GUI) that allows, for example, a physician to manipulate images or models displayed on the display device (e.g., rotating/moving models, sectioning models, hiding portions of the models, defining points or planes relative to models/depictions, etc.), facilitate the determining measurements, etc., the display device 30 may also display such a GUI. In any event, the display device 30 is configured to receive electrical signals from the ECU 28 and to display content represented by the received signals which may be viewed by, for example, a physician.

The user interface device(s) 32 may comprise any number of suitable devices known in the art. For example, and without limitation, the user input device(s) 32 may comprise one or a combination of a touch screen (e.g., LCD touch screen), a keypad, a keyboard, a computer mouse or roller ball, and/or a joystick, to cite a few possibilities. In certain implementations, the display device 30 and user input device 32 may be combined together into a single device such that they are one in the same. Regardless of the particular form the user interface device(s) take, the user input device(s) 32 may be electrically connected or coupled (e.g., via wired or wireless connections) to the ECU 28, and are configured to facilitate communication between a user (e.g., physician) and the system 26, and the ECU 28 thereof, in particular. More particularly, the user interface device(s) 32 may allow a physician to manipulate images or models/depictions displayed on the display device 30 (e.g., hiding portions of models/depictions, defining points or planes relative to models/depictions, rotating/moving models/depictions, etc.), to select or command the determination of measurements relating to anatomical structures represented in models/depictions displayed on the display device 30, etc.

While certain components of the system 26 have been described above, it will be appreciated that in some implementations, the system 26 may include more or fewer components than are included in the arrangement described above. Accordingly, the present disclosure is not intended to be limited to any particular implementation(s) or arrangement(s) of the system 26.

Figure 3:
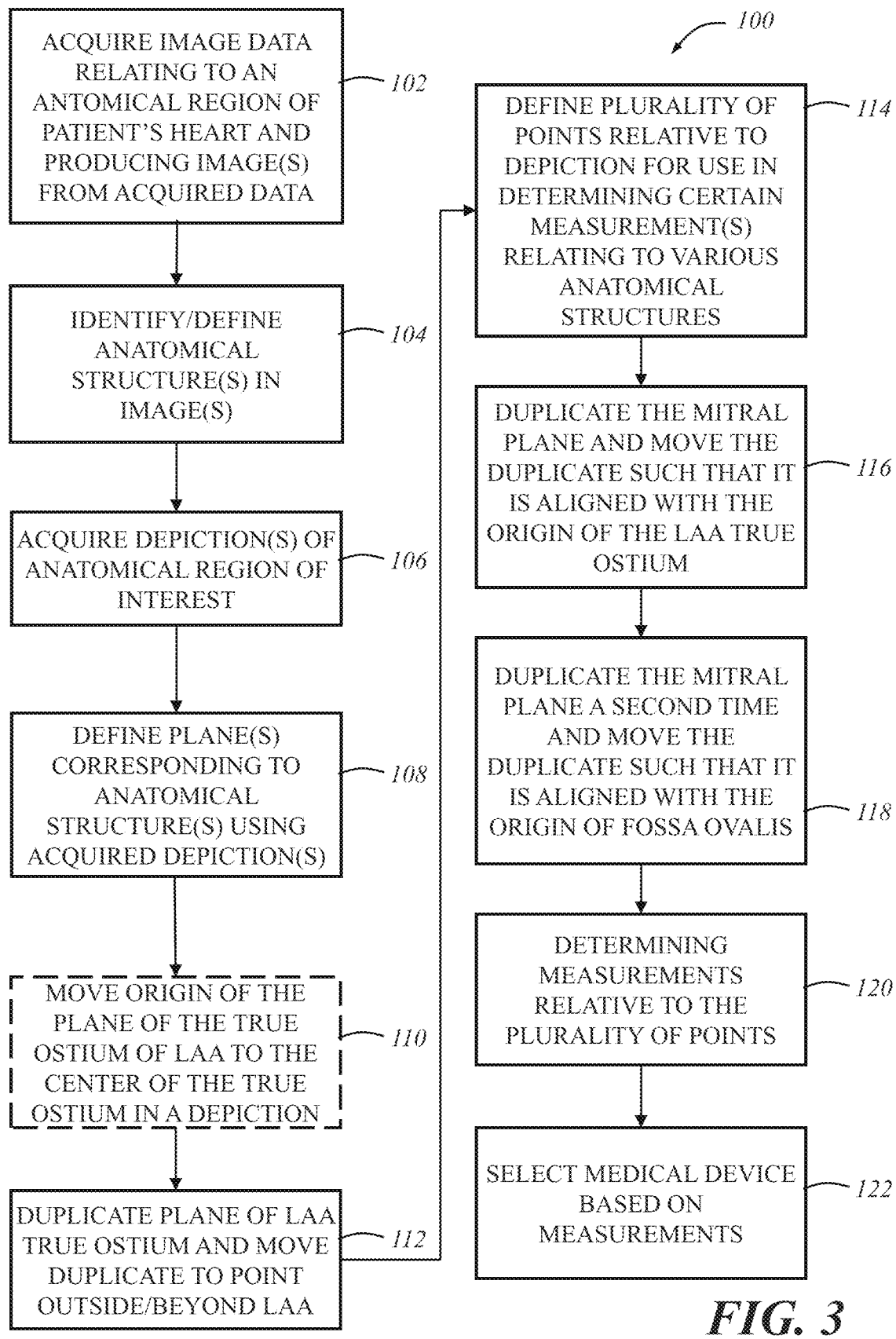
FIG. 3 is a flowchart of an illustrative embodiment of a method that may be used to select or determine a medical device to be used in a medical procedure.

Turning now to FIG. 3, there is shown an illustrative embodiment of a method (method 100) for determining or selecting a medical device to be used in the performance of a medical procedure. More particularly, FIG. 3 illustrates a method of selecting an elongate medical device (e.g., catheter) to be used in the performance of a procedure during which a medical device is delivered to and implanted within a structure of interest located in a particular anatomical region of a patient's body. In a particular illustrative embodiment, the device to be implanted is an LAA occlusion device, and thus, the anatomical region in which the structure of interest (i.e., the LAA) is located includes at least a portion of the patient's heart. For purposes of illustration, the description below will be primarily with respect to selecting a catheter for use in delivering and placing an LAA occlusion device. It will be appreciated, however, that the methodology described herein may be used to evaluate the placement of other devices, some of which may be described below.

In at least some embodiments, all of the steps of method 100 may be performed or carried out by an appropriately or suitably configured system, for example and without limitation, the system 26 described above, either alone or in conjunction with input from a user (e.g., physician). In other embodiments, however, some, but not all, of the steps may be performed or carried out by different systems such that certain steps may be performed by one system (e.g., system 26), and other steps may be performed by one or more other suitable systems. For purposes of illustration, the description below will be primarily with respect to an embodiment wherein the method 100 is performed by the system 26 (and the performance of some or all of the steps of the method 100 is/are facilitated at least in part by software stored in, for example, the memory device 36 of the system 26), either alone or in conjunction with user input. It will be appreciated, however, that the present disclosure is not limited to such an embodiment. Additionally, it will be appreciated that unless otherwise noted, the performance of method 100 is not meant to be limited to any one particular order or sequence of steps, or to any particular component(s) for performing the steps.

In an embodiment, method 100 includes a step 102 of acquiring image data relating to an anatomical region of the patient's heart that may include at least portions of the structure in which a medical device is to be implanted. For instance, in an embodiment where an LAA occlusion device is to be implanted in the LAA of a patient's heart, the image data acquired in step 102 may relate to at least portions of the LAA, the left atrium, the right atrium, and the inferior vena cava (IVC) of the patient's heart.

Figure 4B:
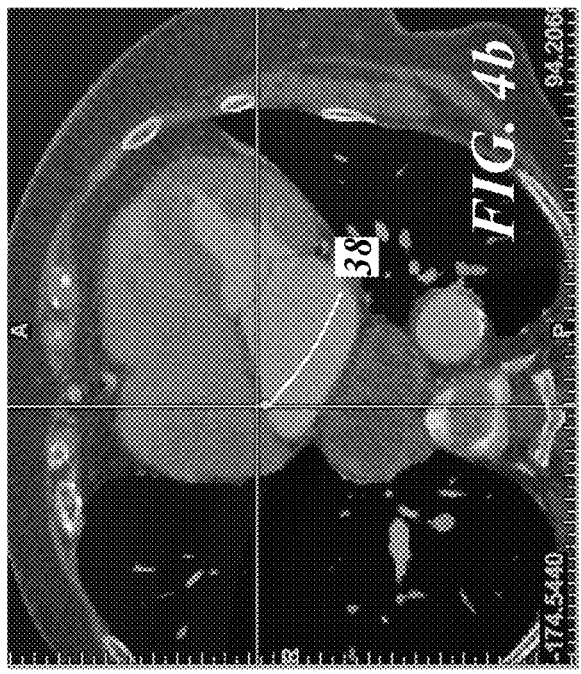
FIGS. 4a-4c are computed tomography (CT) images of portions of a patient's heart that may be used, for example, in the performance of one or more steps of the method illustrated in FIG. 3.
Figure 4A:
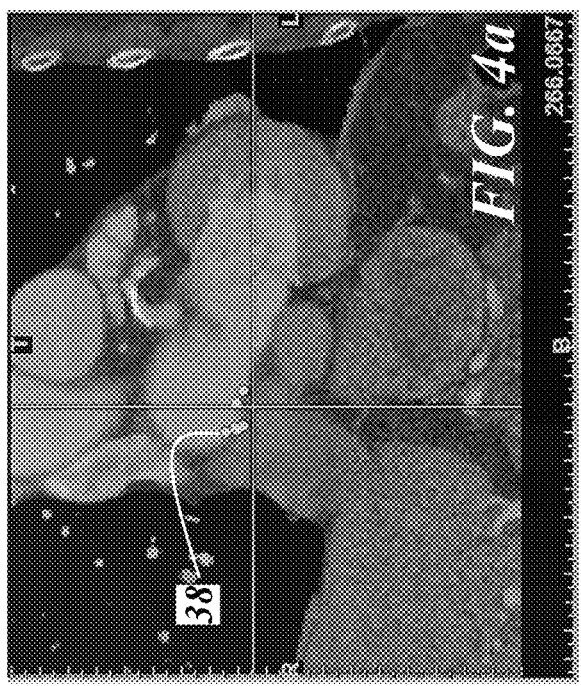
Figure 4C:
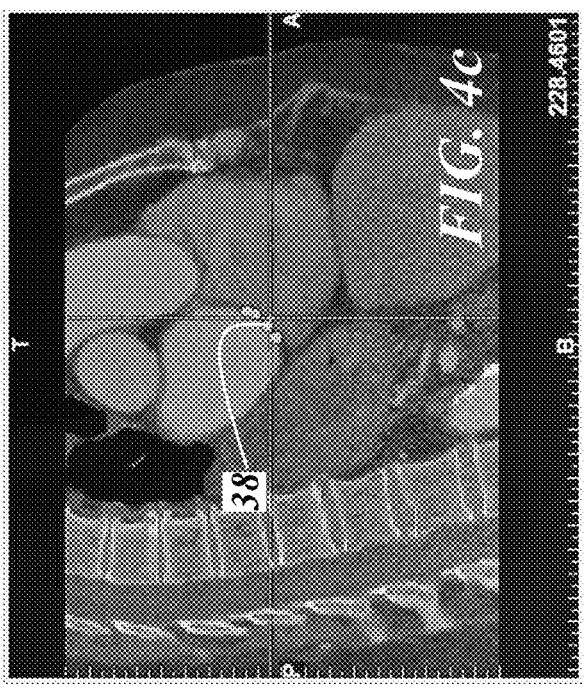

In an illustrative embodiment, the image data comprises computed tomography (CT) image data, and more particularly, two-dimensional (2D) CT data. It will be appreciated, however, that in other embodiments, the image data may comprise data acquired using an imaging modality other than CT, for example, magnetic resonance imaging (MRI), echocardiogram imaging, or another suitable imaging modality. Accordingly, the present disclosure is not intended to be limited to any particular type of image data; however, for purposes of illustration and clarity, the description below will be primarily with respect to an embodiment wherein CT image data is used. Additionally, in an embodiment, the image data may be acquired during the diastolic phase of the patient's cardiac cycle. It will be appreciated, however, that in other embodiments, image data may be additionally or alternatively acquired during the systolic phase of the cardiac cycle. In any event, one or more 2D images or views of the anatomical region to which the image data acquired in step 102 corresponds may be generated or produced from the acquired image data. FIGS. 4a-4c show examples of such images taken along different planes of the patient's heart, wherein FIG. 4a is an image taken along the coronal plane, FIG. 4b is an image taken along the axial plane, and FIG. 4c is an image taken along the sagittal plane.

In a step 104, that or those 2D images may be used to identify and define one or more anatomical structures shown therein. For example, using one or more of the 2D images shown in FIGS. 4a-4c, the fossa ovalis of the patient's heart may be located/identified, and the boundary of the fossa ovalis defined. As shown in FIGS. 4A-4C, the boundary of the fossa ovalis may be defined by placing one or more markers 38 onto the image at locations corresponding to points along the interatrial septum disposed between the left atrium and right atrium. In addition to defining the fossa ovalis, these markers also represent potential insertion points through the interatrial septum for the medical device being selected using method 100. (Because during certain procedures (e.g., LAA-related procedures), the medical device has to cross through the interatrial septum from the right atrium to the left atrium.) In an embodiment, once a marker 38 is placed in one view or image of an anatomical region, it automatically appears in other views/images of the anatomical region if the location corresponding to the marker 38 is visible in that or those other views, as is shown in FIGS. 4a-4c.

An anatomical structure (e.g., the fossa ovalis) may be defined by the placement of the one or more markers 38 in a number of ways. For example, one or more markers 38 may be placed automatically by the ECU 28 of the system 26 (e.g., by the processor 34 of the ECU 28) using, for example, suitable image processing software/techniques. In other embodiments, the one or more markers 38 may be placed by a user (e.g., physician). More specifically, a 2D image may be displayed on the display device 30 and the user may place one or more markers 38 thereon using the user interface device(s) 32 of the system 26. For example, the user may manipulate a computer mouse to move a cursor to a desired location in the displayed image and "click" the mouse to place a marker 38.

While certain techniques or implementations for defining an anatomical structure of interest have been provided above, it will be appreciated that any suitable technique(s) for doing so may be used. Accordingly, the present disclosure is not intended to be limited to any particular technique(s) for doing so.

In any event, the performance of steps 102 and 104 may be facilitated at least in part by software stored in, for example, the memory device 36 of the system 26. In an embodiment, this software may comprise a software program commercially available from Materialise NV under the name Mimics®; though any other suitable software may certainly be used instead.

Figure 5:
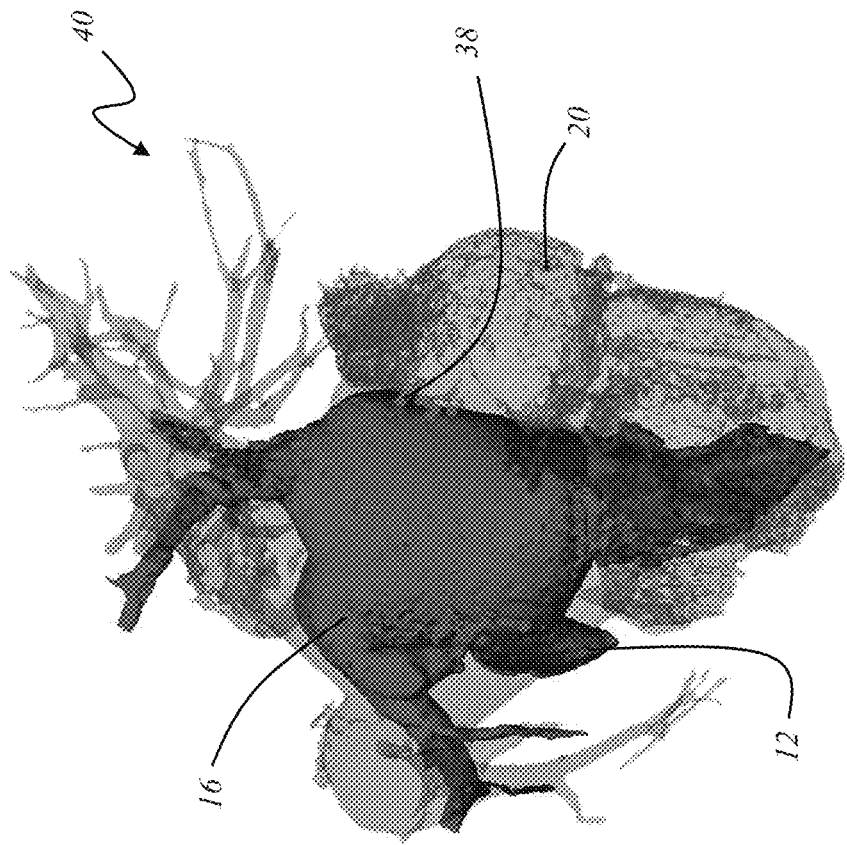
FIGS. 5-13 are various depictions of models that may be used in the performance one or more steps of the method illustrated in FIG. 3, and show an illustrative embodiment of how the method illustrated in FIG. 3 may be carried out.

Following step 102, and in at least some embodiments, following both step 102 and step 104, method 100 may proceed to a step 106 of acquiring one or more depictions/models of an anatomical region of interest of the patient's body. Accordingly, as shown in FIG. 5, in an embodiment, step 106 comprises acquiring one or more depictions or models 40 of at least a portion of the patient's heart that includes, among other structures, the LAA 12, the left atrium 16, and the right atrium 20. The model(s) or depiction(s) 40 acquired in step 106 may also include markers used in step 104 to define one or more structures of interest (e.g., the boundary of the fossa ovalis). Accordingly, the depiction shown in FIG. 5 includes at least some of the markers 38 placed in step 104 to define the fossa ovalis of the patient's heart. In an embodiment, the depiction(s) 40 comprise one or more computer-generated models of the anatomical region of interest, for example, one or more multi-dimensional models (e.g., one or more three-dimensional (3D) models). For purposes of illustration and clarity, the description below will be with respect to an embodiment wherein the acquired depiction(s) 40 comprise a 3D model of the anatomical region of interest. It will be appreciated, however, that in other embodiments, different types of depictions may be used (e.g., computer-generated models other than 3D models).

In an embodiment where a 3D model is acquired in step 106, that model may be acquired in a number of ways. One way is by obtaining a previously-generated model from a memory device, for example, the memory device 36 of the system 26. Another way is by generating the model from image data, for example 2D image data. In the latter instance, the image data may be the same image data acquired in step 102 or alternatively may be other image data (e.g., 2D CT image data) acquired as part of step 106. In either instance, the model may be generated using techniques well known in the art, such as, for example, that or those techniques described in U.S. Patent Publication No. 2016/0038246 filed on Aug. 7, 2015, the entire contents of which are incorporated herein by reference; and in an embodiment, may be generated by, for example, the ECU 28 of the system 26, and the processor 34 thereof, in particular. Accordingly, it will be appreciated that the present disclosure is not intended to be limited to any particular way(s) of acquiring the one or more depictions in step 106.

Regardless of how the one or more depictions/models 40 is/are acquired in step 106, in an embodiment, the acquired depictions 40 (e.g., the single 3D model) may be generated by and/or copied into or used by a suitable software program for performing the steps below. An example of such software is that commercially available from Materialise NV under the name 3-Matic STL. As briefly described above, if applicable, representations of one or more markers 38 placed in step 104 to define an aspect (e.g., boundary) of one or more anatomical structures may also be imported into the model/depiction 40 acquired in step 106.

In at least some embodiments, the depiction(s) 40 acquired in step 106 may be such that portions of the depiction representative of different anatomical structures may be selectively hidden so as to provide, for example, a better or clearer view of other anatomical structures. For example, the depiction shown in FIG. 5 includes the LAA 12, the left atrium 16, and the right atrium 20. In the depictions shown in, for example, FIG. 6, however, the right atrium is hidden so as to provide a better, clearer view of the LAA 12 and left atrium 16. Accordingly, the present disclosure is not intended to be limited to the acquisition of any particular type of depiction(s) (e.g., static or dynamic) in step 106.

Figure 6:
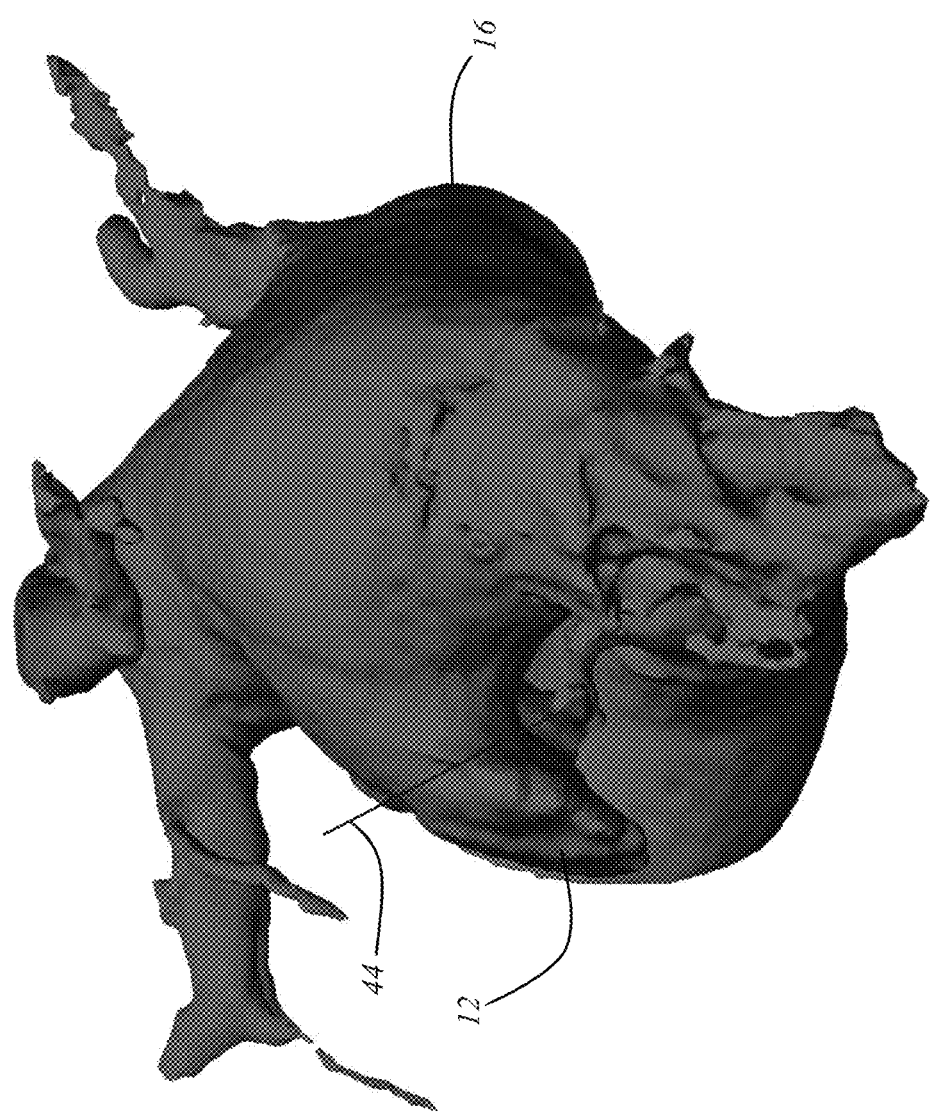
Figure 7:
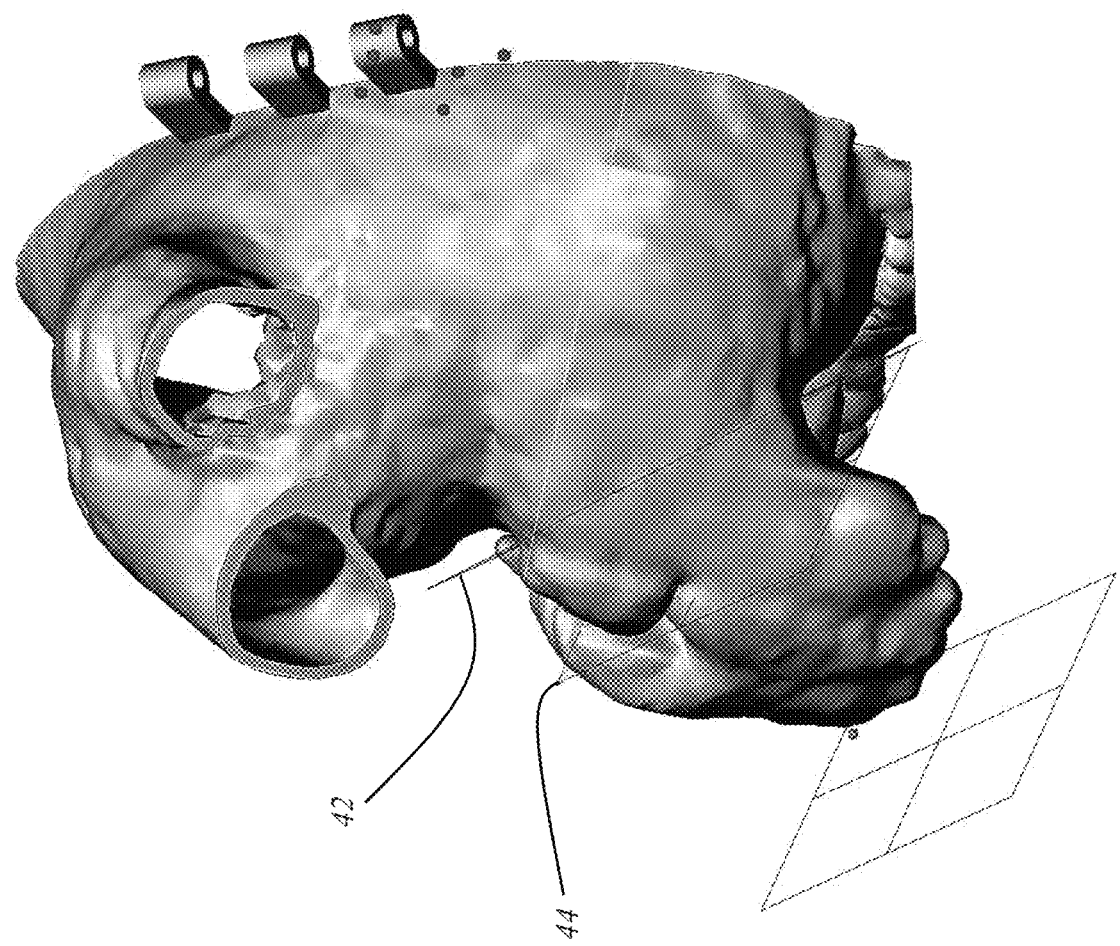

Once a depiction of the anatomical region of interest is acquired in step 106, the method 100 moves to a step 108 of using the acquired depiction 40 to define one or more planes corresponding to one or more anatomical structures shown in the acquired depiction 40. For example, in an embodiment such as that illustrated in FIG. 6, step 108 comprises defining a plane that contains the ostium of the LAA 12. In an embodiment, the plane being defined does not correspond to or contain what is conventionally considered by those of ordinary skill in the art to be the ostium of the LAA (referred to below as the "false ostium"), which is the opening of the LAA immediately adjacent the left atrium. Rather, the "ostium" of the LAA for purposes of this disclosure (referred to below as the "true ostium") may comprise the portion or point of the LAA that has the greatest circumference/perimeter, that is distal of the conventional "ostium" of the LAA (i.e., further into the LAA and away from the left atrium than the conventional ostium), and that has a plane that is perpendicular to the centroid of the LAA. For purposes of illustration, FIG. 7 illustrates a plane 42 containing the false ostium and a plane 44 containing the true ostium (plane 44 containing the true ostium is also shown in FIG. 6).

The plane 44 of the true ostium may be defined in a number of ways. One way is by tracing the perimeter of the LAA 12 at its largest point. Another way is by placing and positioning a cross-sectional plane at the desired location in or on the depiction 40. In either case, the plane 44 may be defined automatically by the ECU 28 of the system 26 (e.g., by the processor 34 of the ECU 28) using, for example, suitable image processing software/techniques. Alternatively, the plane 44 may be defined by a user (e.g., physician) manipulating the user interface device(s) 32 of the system 26. More specifically, the depiction 40 acquired in step 106 may be displayed on the display device 30 and the user may trace the perimeter of the LAA 12 or place a cross-sectional plane onto the depiction 40 using the user interface device(s) 32. For example, the user may manipulate a computer mouse to move a cursor to a desired location in the displayed depiction 40 and "click" the mouse to place a cross-sectional plane at that location. Regardless of how the plane 44 is defined, in an embodiment, a representation of the defined plane 44 may be displayed on the depiction 40 for the user to view, as shown in FIGS. 6 and 7.

While certain techniques or implementations for defining the true ostium plane 44 of the LAA 12 have been provided above, it will be appreciated that any suitable technique(s) for doing so may be used. Accordingly, the present disclosure is not intended to be limited to any particular technique(s) for doing so.

Another plane that may be defined in step 108 is a plane that contains the mitral annulus of the patient's heart; that plane being referred to herein as the "mitral plane." Alternatively, the mitral plane may be defined in a step of method 100 performed before or after step 108, or may not be defined at all. In an instance where the mitral plane is defined, it may be done so in a number of ways using any number of techniques known in the art. For example, in one embodiment, step 108 may comprise acquiring image data relating to an anatomical region of the patient's heart that includes, for example, the left ventricle, left atrium, and aorta of the patient's heart. The image data may be the same image data acquired in step 102 or comprise different image data. In either instance, the image data may comprise CT image data, and more particularly, 2D CT image data. It will be appreciated, however, that in other embodiments, the image data may comprise data acquired using a suitable imaging modality other than CT, for example, one or more of those imaging modalities identified elsewhere herein. Accordingly, the present disclosure is not intended to be limited to any particular type of image data. However, for the purposes of illustration and clarity, the description below will be with respect to the use of CT data. Additionally, in an embodiment, image data may be acquired for both the diastolic and systolic phases of the cardiac cycle, and in such an embodiment, the mitral plane may be defined for each phase. Alternatively, data may be acquired and the mitral plane defined for only one of the diastolic and systolic phases.

In an embodiment, one or more 2D images generated from the acquired CT image data may be used to define the mitral plane. More particularly, a 2D image may be used to define a certain number of points (e.g., three (3) points) that may be used to define the mitral plane. In an embodiment, one or more predetermined landmarks (e.g., anatomical landmarks) may be used to identify/define the plane-defining points. The particular landmarks used may depend, at least in part, on the nature of structure proximate the mitral annulus. For example, in an instance wherein the structure is a native mitral valve, the landmarks may include areas of calcification and/or leaflet tips and/or insertion points at the mitral annulus of the native valve, to cite few possibilities. In an instance wherein the structure comprises a previously-implanted device or object, for example, a mitral ring, the landmarks may comprise that device or at least certain portions thereof. Finally, in an instance wherein the structure comprises a previously-implanted prosthetic mitral valve, the landmarks may comprise portions of the previously-implanted valve, for example, the tips of the struts of the previously-implanted valve. In any event, the plane-defining points may be defined or identified in a number of ways.

In one embodiment, the points may be defined automatically by the ECU 28 of the system 26 (e.g., by the processor 34 of the ECU 28) using, for example, suitable image processing software/techniques. In other embodiments, the points may be defined by a user (e.g., physician). More specifically, the 2D image may be displayed on the display device 30 and the user may define the plane-defining points using the user interface device(s) 32 of the system 26. For example, the user may manipulate a computer mouse to move a cursor to a desired location on the image and to "click" the mouse to define a point. In any event, once the plane-defining points are defined, a plane containing all of the defined points can be defined as the mitral plane. In at least some embodiments, the mitral plane can be represented on a 2D image by, for example, a spline. While certain techniques or implementations for defining the mitral plane-defining points, and thus, defining the mitral plane itself have been provided above, it will be appreciated that any suitable technique(s) for doing so may be used. Accordingly, the present disclosure is not intended to be limited to any particular technique(s) for doing so.

In another embodiment, rather than using a 2D image to define the mitral plane, the depiction 40 acquired in step 106 may be used. For example, a cross-sectional plane may be positioned at the desired location in or on the depiction 40. In such an embodiment, the mitral plane may be defined automatically by the ECU 28 of the system 26 (e.g., by the processor 34 of the ECU 28) using, for example, suitable image processing software/techniques. Alternatively, the plane may be defined by a user (e.g., physician) manipulating the user interface device(s) 32 of the system 26. More specifically, the depiction 40 acquired in step 106 may be displayed on the display device 30 and the user may manipulate a computer mouse to move a cursor to a desired location in the displayed depiction 40 and "click" the mouse to place a cross-sectional plane at that location. In such an instance, in an embodiment wherein portions of the depiction 40 acquired in step 106 may be hidden, structures that were previously hidden during the performance of other steps of method 100 may be displayed in order to facilitate the performance of step 108 (e.g., the left ventricle, the mitral valve, the mitral annulus, etc.).

Figure 12:
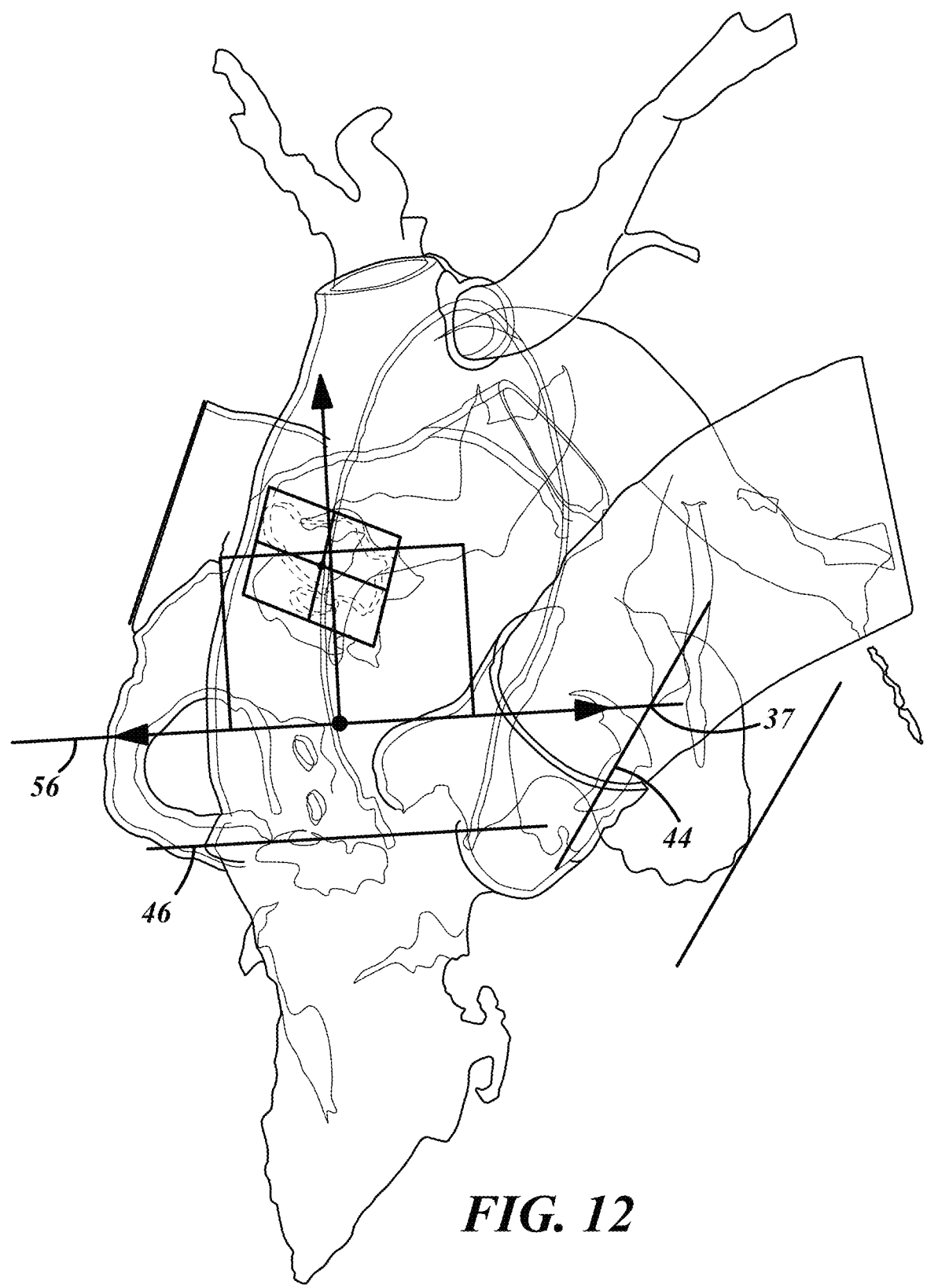

Regardless of how the mitral plane is defined, in an embodiment, a representation of the defined mitral plane may be displayed on the depiction 40, as shown, for example, in FIG. 12 wherein reference numeral 46 corresponds to the defined mitral plane. While certain techniques or implementations for defining the mitral plane 46 have been provided above, it will be appreciated that any suitable technique(s) for doing so may be used. Accordingly, the present disclosure is not intended to be limited to any particular technique(s) for doing so. Additionally, the performance of step 108 may be facilitated at least in part by software stored in, for example, the memory device 36 of the system 26. In an embodiment, this software may comprise a software program commercially available from Materialise NV under the name 3Matic STL or Mimics®; though any other suitable software may certainly be used instead.

While the description of step 108 has thus far been with respect to the defining of planes containing or corresponding to certain specific anatomical structures, it will be appreciated that in other embodiments, additional or alternative planes may be defined. Accordingly, the present disclosure is not necessarily limited to the defining of any particular planes in step 108, but rather any number of suitable planes may be defined in step 108.

Turning back to FIG. 3, in an embodiment, the method 100 may further include an optional step 110 of moving the true ostium plane 44 defined in step 108 along the object coordinate system (X&Y) until the origin of the plane 44 is in the center of the true ostium of the LAA 12. In an embodiment, a hollow body blood volume model may be used to perform this step. In an embodiment, step 110 may be performed automatically by the ECU 28 of the system 26 (e.g., by the processor 34 of the ECU 28) using, for example, suitable image processing software/techniques. Alternatively, the step 110 may be performed by a user (e.g., physician) manipulating the user interface device(s) 32 of the system 26. More specifically, the user may manipulate a computer mouse to move the plane 44 to a desired point or location corresponding to the center of the true ostium of the LAA in the displayed depiction.

Figure 8:
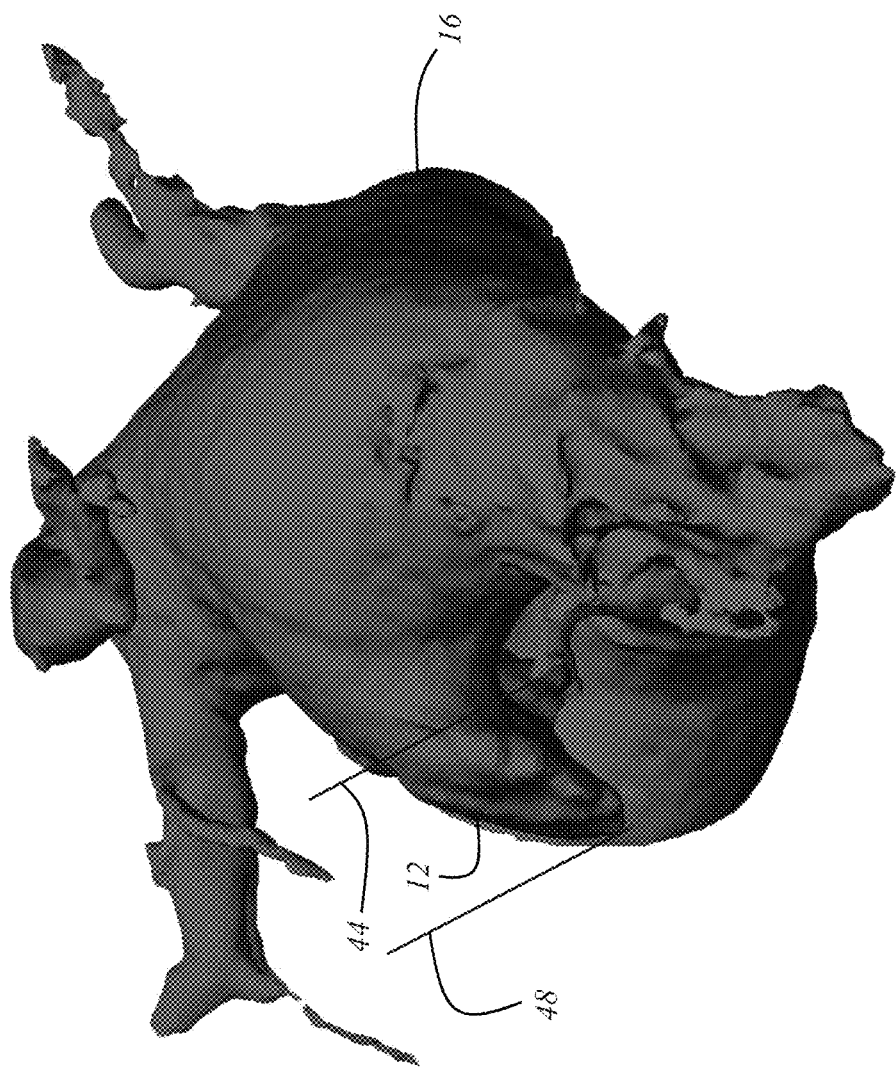

Whether or not method 100 includes step 110, and with reference to FIGS. 3 and 8, in an embodiment method 100 includes a step 112 of duplicating the true ostium plane 44 to create a duplicate plane 48, and moving the duplicate plane 48 along the objects coordinate system perpendicular to the plane 44 (e.g., in the Z direction) to a point that is outside or beyond the LAA 12 in the depiction 40. The plane 48 may hereinafter be referred to as the perpendicular offset plane 48 or the offset true ostium plane 48. In an embodiment, the distance between the LAA 12 and the point outside or beyond the LAA 12 may be on the order of a few centimeters, though the present disclosure is not intended to be limited to any particular distance. In an embodiment, step 112 may be performed automatically by the ECU 28 of the system 26 (e.g., by the processor 34 of the ECU 28) using, for example, suitable image processing software/techniques. Alternatively, the step 112 may be performed by a user (e.g., physician) manipulating the user interface device(s) 32 of the system 26. More specifically, the user may manipulate a computer mouse to cause the plane 44 to be duplicated to and to then move the duplicate plane 48 to a desired point or location beyond the LAA 12 in the displayed depiction 40, thereby establishing the perpendicular offset plane 48.

In an embodiment, method 100 may further include a step 114 of defining a plurality of points relative to the depiction 40 (i.e., in/on or in the vicinity of the depiction 40), two or more which will be used to determine or calculate one or more measurements relative to one or more anatomical structures that will, in turn, be used in the selection of a medical device to be used in the performance of a medical procedure.

Figure 9:
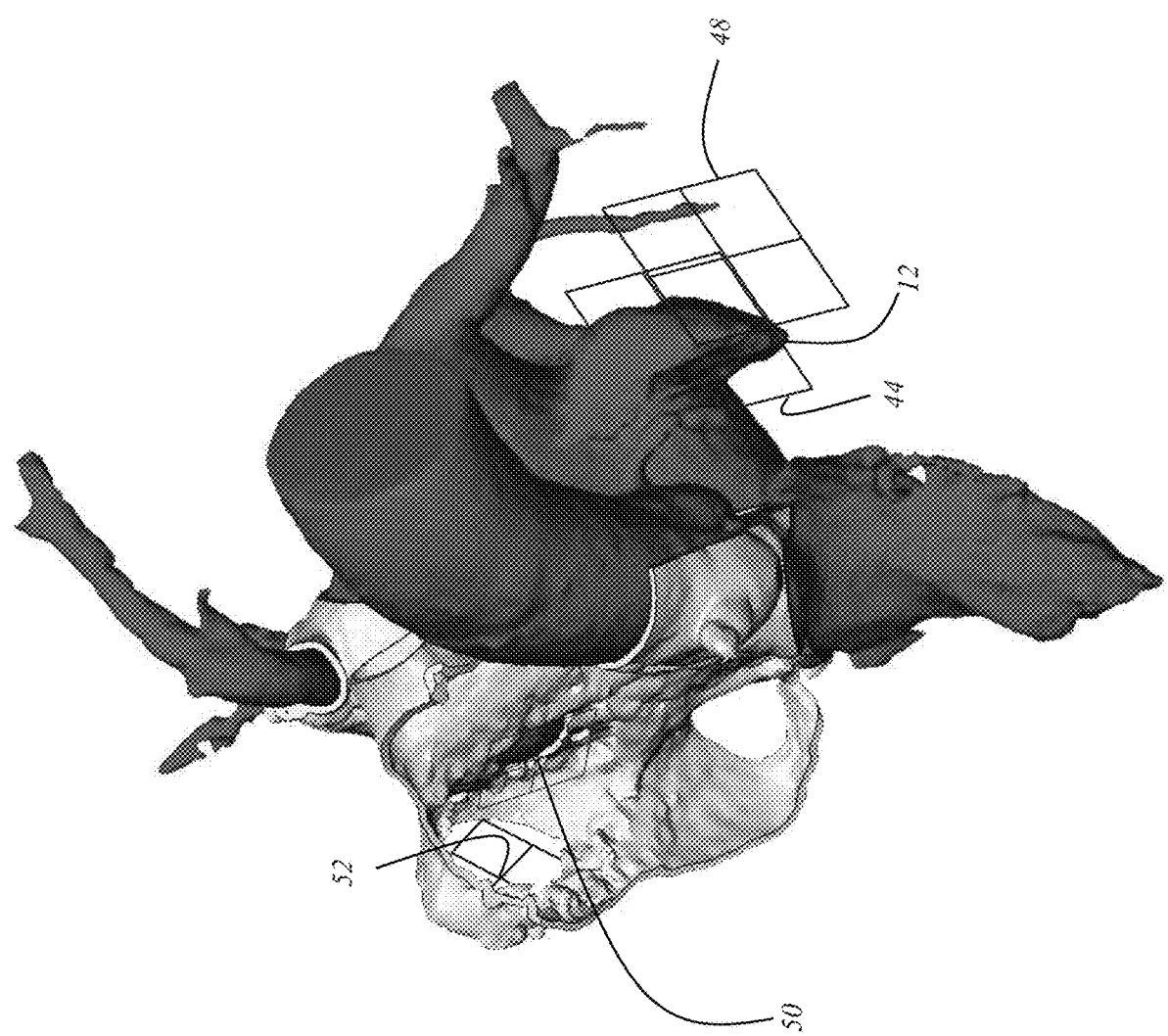

In an embodiment such as that illustrated in FIG. 9, step 114 includes a number of substeps, including identifying and defining the origin(s) of one or more planes. For example, in an illustrative embodiment, step 114 includes a sub step of identifying and defining the origin of one or both of the true ostium plane 44 and the perpendicular offset plane 48. Step 114 may also include a sub step of identifying and defining the origin of a plane containing the fossa ovalis (i.e., the centroid of the fossa ovalis (also referred to as the origin of the fossa ovalis plane)) and/or the origin of a plane containing the ostium of the IVC (i.e., the centroid of the IVC ostium (also referred to as the origin of the IVC ostium plane)), which are respectively identified in FIG. 9 by reference numerals 50, 52. In other embodiments, the origin(s) of one or more planes in addition to or other than those mentioned above may be identified and defined. In any event, each of the substeps of step 114 may be performed in a number of ways.

Figure 10:
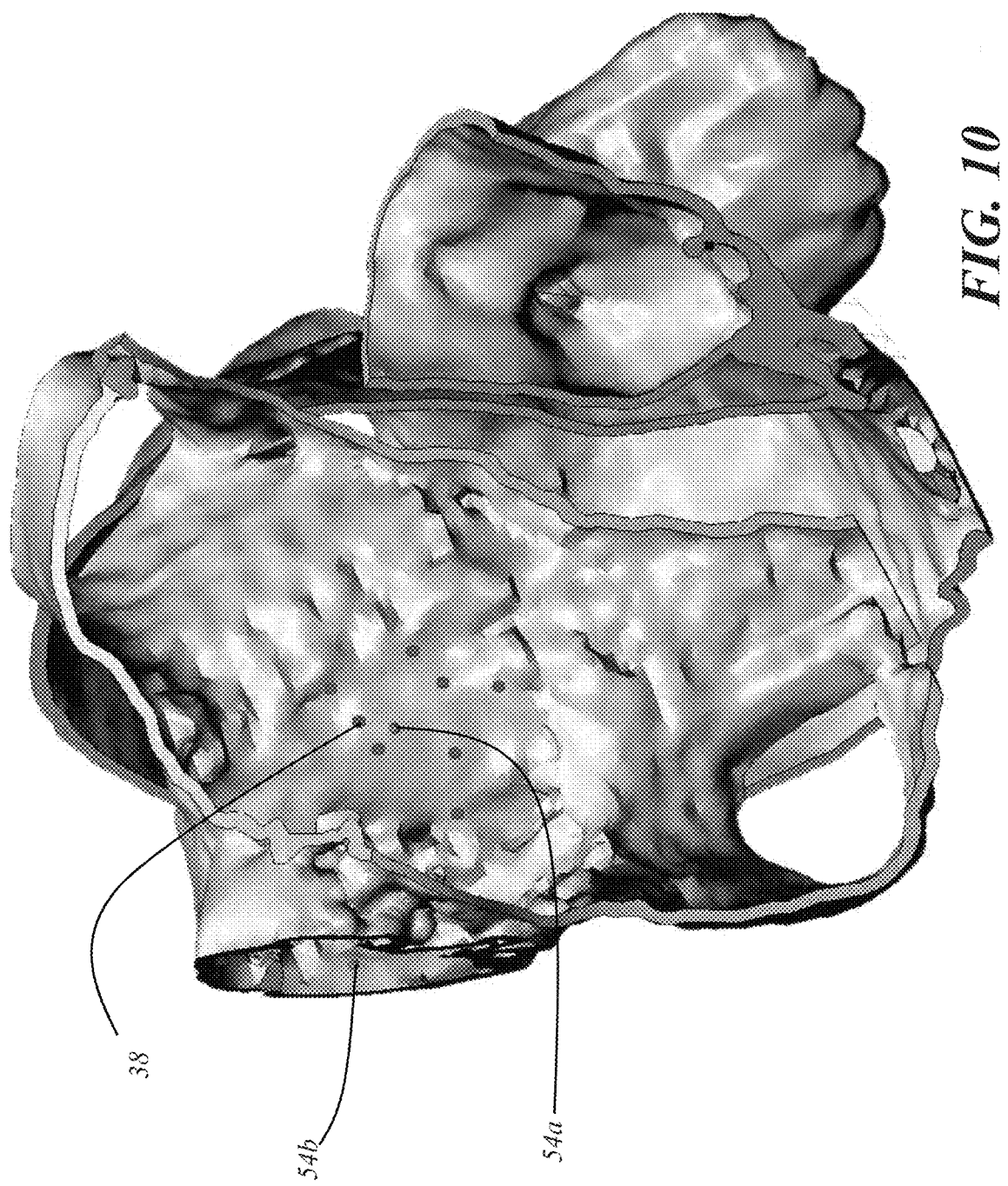

One way is by placing a point or marker 54 on or at the origin/centroid of the planes/structures of interest, as shown in FIG. 10 wherein marker 54a corresponds to the origin/centroid of the fossa ovalis and marker 54b corresponds to the origin/centroid of the IVC ostium. In an embodiment, one or more of the sub steps may be performed automatically by the ECU 28 of the system 26 (e.g., by the processor 34 of the ECU 28) using, for example, suitable image processing software/techniques. Alternatively, one or more of the substeps may be performed by a user (e.g., physician) manipulating the user interface device(s) 32 of the system 26.

Figure 11:
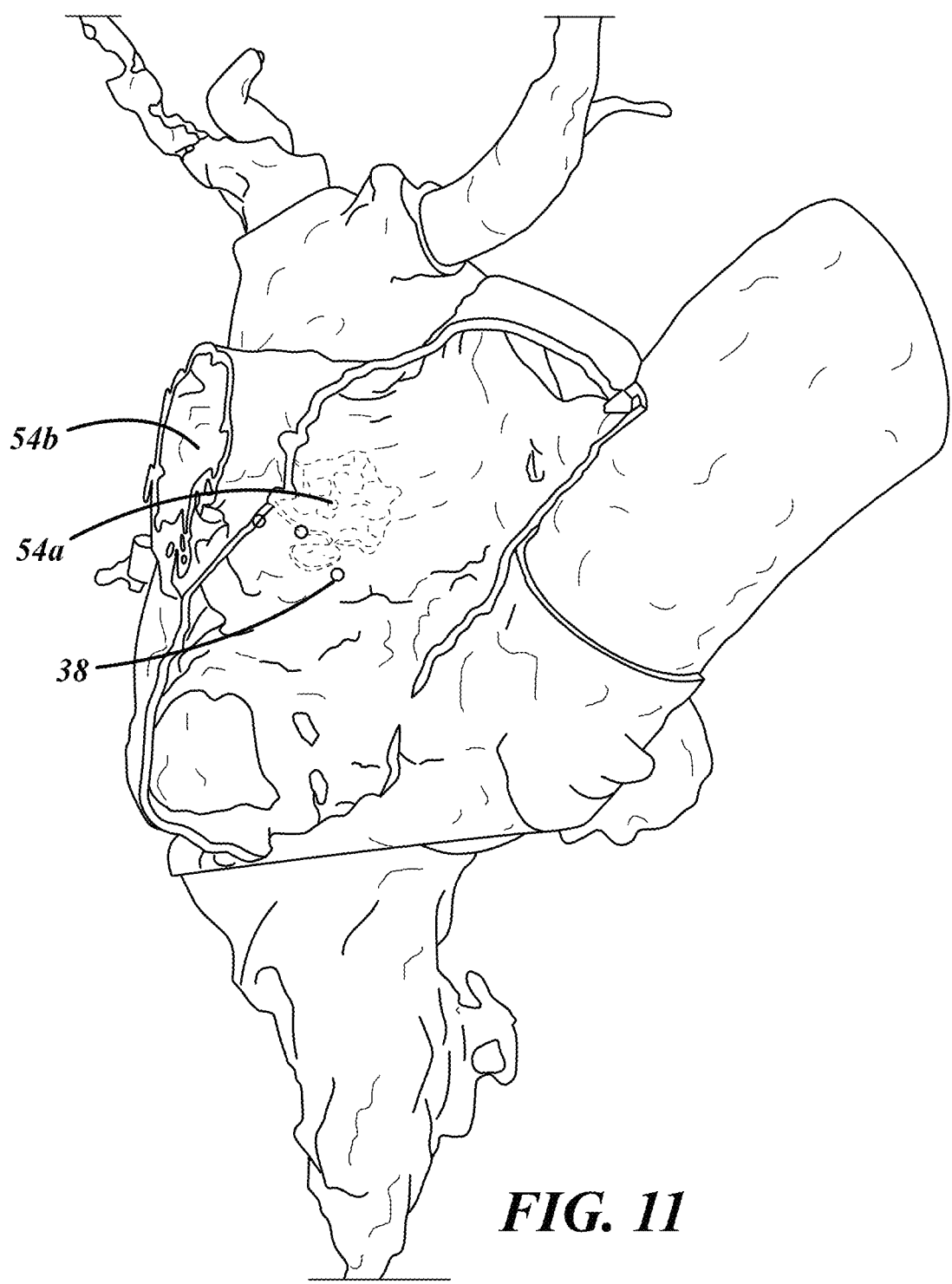

More specifically, the user may manipulate a computer mouse to rotate or move the depiction 40 displayed on the display 30 and/or move a cursor to a desired location in the displayed depiction 40 corresponding to the desired origin/centroid and "click" the mouse to place a point or marker at that location. As it relates to identifying/defining the origin of the plane that contains the fossa ovalis, in an embodiment such as that shown in FIG. 10, the markers 38 corresponding to the boundary of the fossa ovalis defined, for example, in step 104 may be used to guide the identification and definition of the origin/centroid 54a. In another embodiment such as that shown in FIG. 11, a thickness analysis tool may be used to identify/define the origin/centroid 54a of the fossa ovalis. More specifically, such a tool may be used to identify the thinnest or narrowest area of the fossa ovalis. For example, the tool may generate a color map wherein different colors represent different thicknesses (e.g., red being the thinnest and green is the thickest). Using this map, the thinnest point can be identified and considered to be the origin/centroid 54a of the fossa ovalis, and a plane including that origin/centroid 54a can be defined. In another embodiment, the plane may be defined using image data, for example CT data. More particularly, using a 2D CT image, a point where the left and right atrium meet can be identified in an image and a plane can be defined that includes that point. Accordingly, it will be appreciated that any number of techniques may be used.

Accordingly, it will be appreciated that the present disclosure is not intended to be limited to any particular way or technique of performing step 114. Additionally, it will be appreciated in view of, for example, FIGS. 5, 6, and 8 that in some embodiments wherein portions of the depiction 40 acquired in step 106 may be hidden, structures that were previously hidden during the performance of other steps of method 100 may be displayed in order to facilitate the performance of step(s) 114.

In at least some embodiments, the markers 54 corresponding to the identified/defined origins/centroids may be displayed on the depiction for the user to view, regardless of how the origins/centroids are identified/defined.

While the description above is with respect to the identification/definition of the origins/centroids of certain specific structures/planes, it will be appreciated that in other embodiments, such as, for example, those described below, the origin(s)/centroid(s) of additional or alternate structures/planes may be identified/defined. Accordingly, the present disclosure is not intended to be limited to the identification/definition of the origin(s)/centroid(s) of any particular structures/planes in step 114.

As shown in FIG. 3 and with reference to FIG. 12, in an embodiment, method 100 further includes a step 116 of duplicating the mitral plane 46 defined in step 112 and moving the duplicate plane or a representation of the plane 46 (represented by reference numeral 56 in FIG. 12) along the objects coordinate system perpendicular to the plane 46 (e.g., in the Z direction) to a point such that the representation 56 of the plane 46 is both offset from the mitral plane 46 and aligned or level with the origin of the true ostium plane 44 (represented by reference numeral 57), as is shown in FIG. 12. The representation 56 comprising an offset mitral plane.

Figure 13:
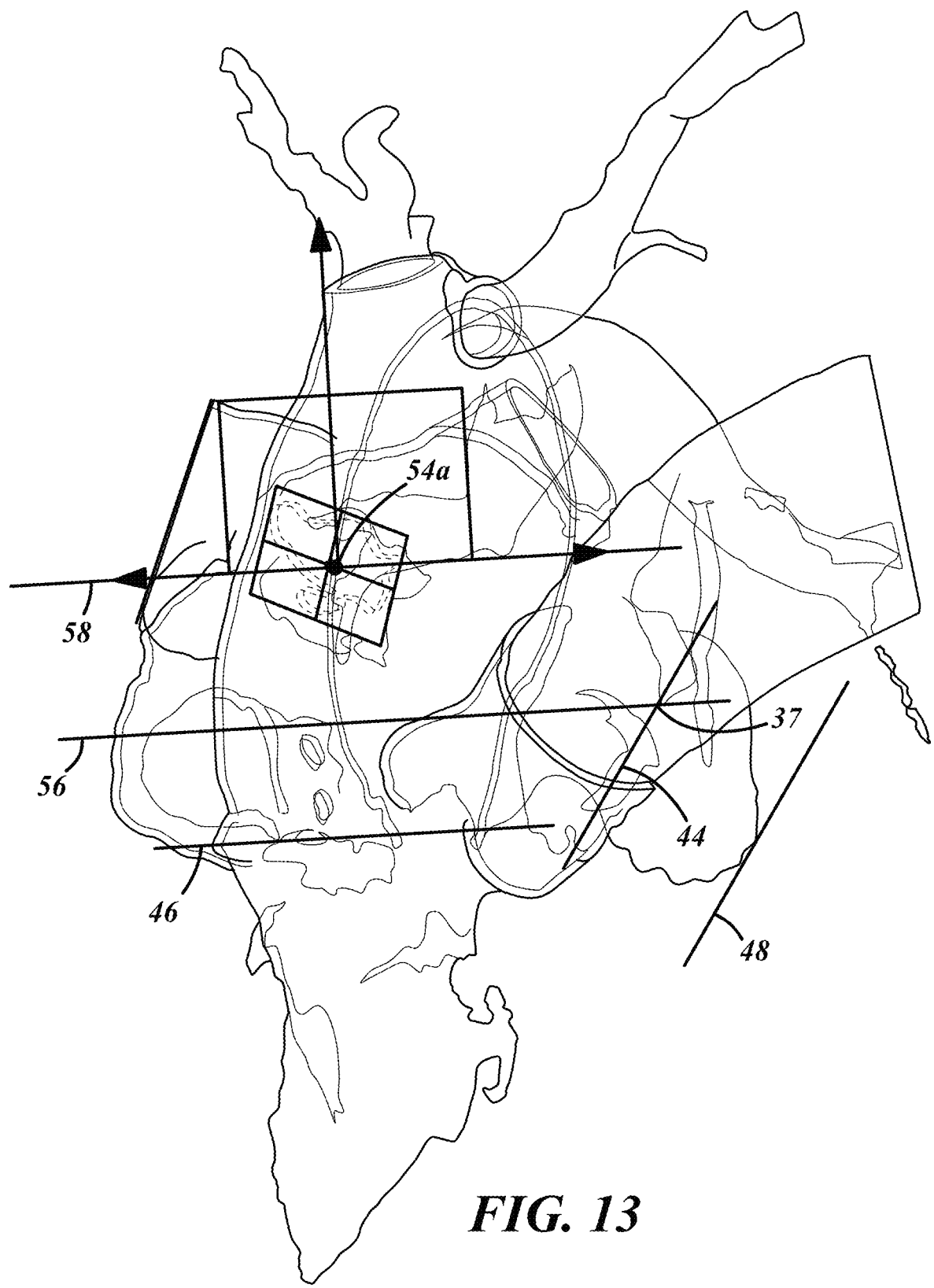

In at least some embodiments, method 100 may further include a step 118 of duplicating the mitral plane 46 a second time and moving the second duplicate plane or a representation of the plane 46 (represented by reference numeral 58 in FIG. 13) along the objects coordinate system perpendicular to the plane 46 (e.g., in the Z direction) to a point such that the representation 58 of the plane 46 is both offset from the mitral plane 46 and the representation 56 of the plane 46, and is also aligned or level with the origin/centroid 54a of the fossa ovalis, as is shown in FIG. 13. The representation 58 also comprising an offset mitral plane.

Whether method 100 includes one or both of steps 116, 118, one or both of those steps may be performed automatically by the ECU 28 of the system 26 (e.g., by the processor 34 of the ECU 28) using, for example, suitable image processing software/techniques. Alternatively, one or both of steps 116, 118 may be performed by a user (e.g., physician) manipulating the user interface device(s) 32 of the system 26. More specifically, the user may manipulate a computer mouse to cause the mitral plane 46 shown on the depiction 40 displayed on the display 30 of the system 26 to be duplicated one or more times, and to then move (e.g., drag) the duplicate mitral plane(s) (i.e., representation 56 and/or 58) to the desired point(s) or location(s) to establish one or more offset mitral planes. Additionally, it will be appreciated that in some embodiments wherein portions of the depiction acquired in step 106 may be hidden, structures that were previously hidden during the performance of other steps of method 100 may be displayed in order to facilitate the performance of step(s) 116, 118.

Using, at least in part, the points identified or defined in step 114, method 100 comprises a step 120 of determining or calculating various measurements, for example, distances between two or more of the defined points and/or angles defined by a combination of points. For example, and with reference to FIG. 14, in one embodiment wherein method 100 is being used to determine or select a medical device (e.g., catheter) to be used in an LAA-related procedure (e.g., to deliver and place an LAA occlusion device), one or more of the following five (5) measurements may be determined, and one or more of the determined measurements may be used to determine or select a medical device.

Figure 14:
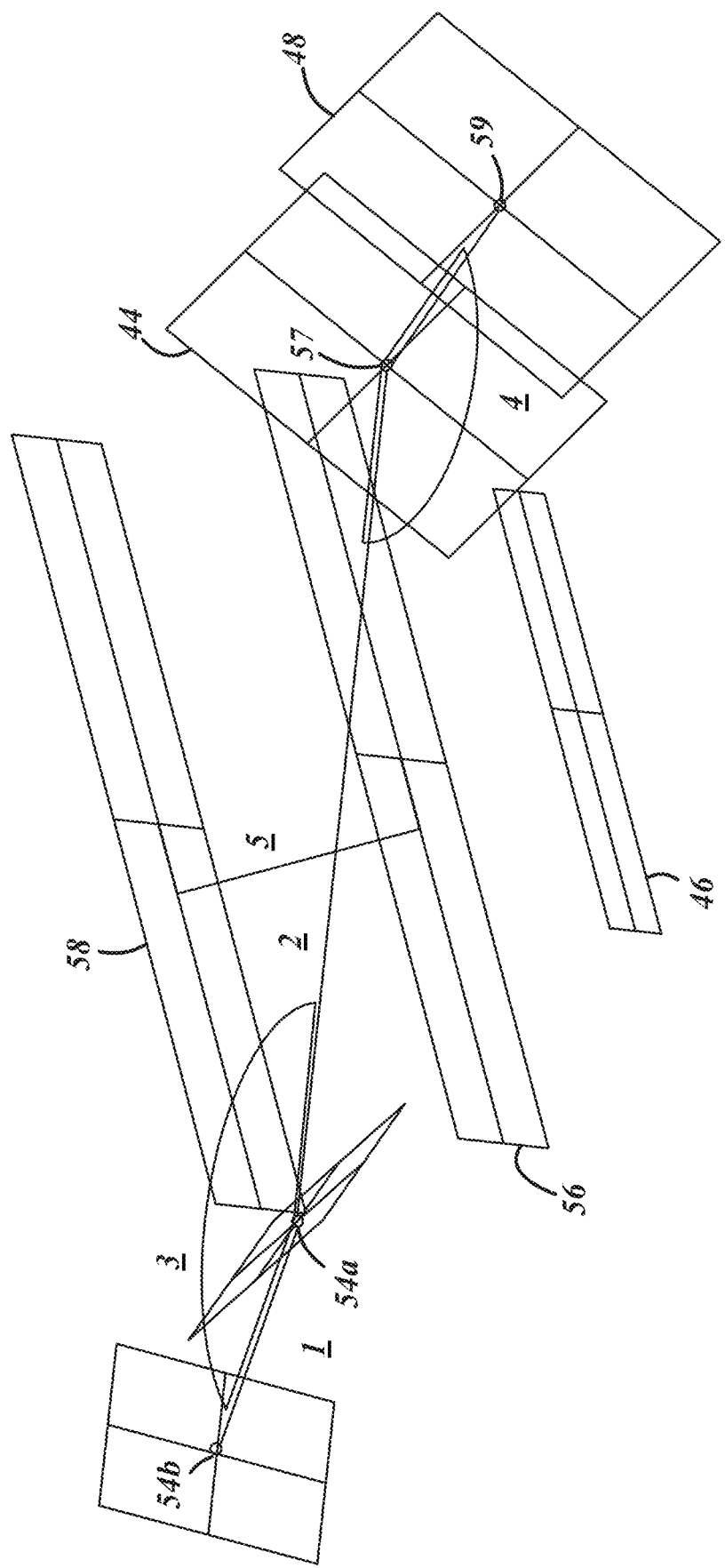
FIGS. 14-17 are diagrammatic and schematic views of various measurements that may be determined in one or more steps of the method illustrated in FIG. 3, which may be used in one or more other steps of the method illustrated in FIG. 3. It will be appreciated that any particular measurements shown in the figures are provided for illustrative purposes only and are not meant to be limiting in any way.

A first measurement, identified as measurement "1" in FIG. 14, is the distance between the point 54b corresponding to the origin/centroid of the IVC ostium (i.e., origin of a plane containing the IVC ostium) and the point 54a corresponding to the origin/centroid of the fossa ovalis (i.e., origin of a plane containing the fossa ovalis).

A second measurement, identified as measurement "2" in FIG. 14, is the distance between the point 54a corresponding to the origin/centroid of the fossa ovalis and the point 57 corresponding to the origin of the plane 44 of the true ostium.

A third measurement, identified as measurement "3" in FIG. 14, is the angle formed by the point 54b corresponding to the origin/centroid of the IVC ostium, the point 54a corresponding to the origin/centroid of the fossa ovalis, and the point 57 corresponding to the origin of the plane 44 of the true LAA ostium.

A fourth measurement, identified as measurement "4" in FIG. 14, is the angle formed by the point 54a corresponding to the origin/centroid of the fossa ovalis, the point 57 corresponding to the origin of the plane 44 of the true LAA ostium, and a point 59 corresponding to the origin of the offset LAA true ostium plane 48 (also referred to as the offset true ostium plane 48).

And a fifth measurement, identified as measurement "5" in FIG. 14, is the distance between the first and second offset mitral planes 56, 58 that intersect with the true ostium plane 44 and the origin/centroid 54a of the fossa ovalis, respectively.

It will be appreciated that while certain specific measurements are identified and discussed above, in other embodiments, one or more measurements in addition to or instead of those described above may be determined and used as described below.

Figure 15:
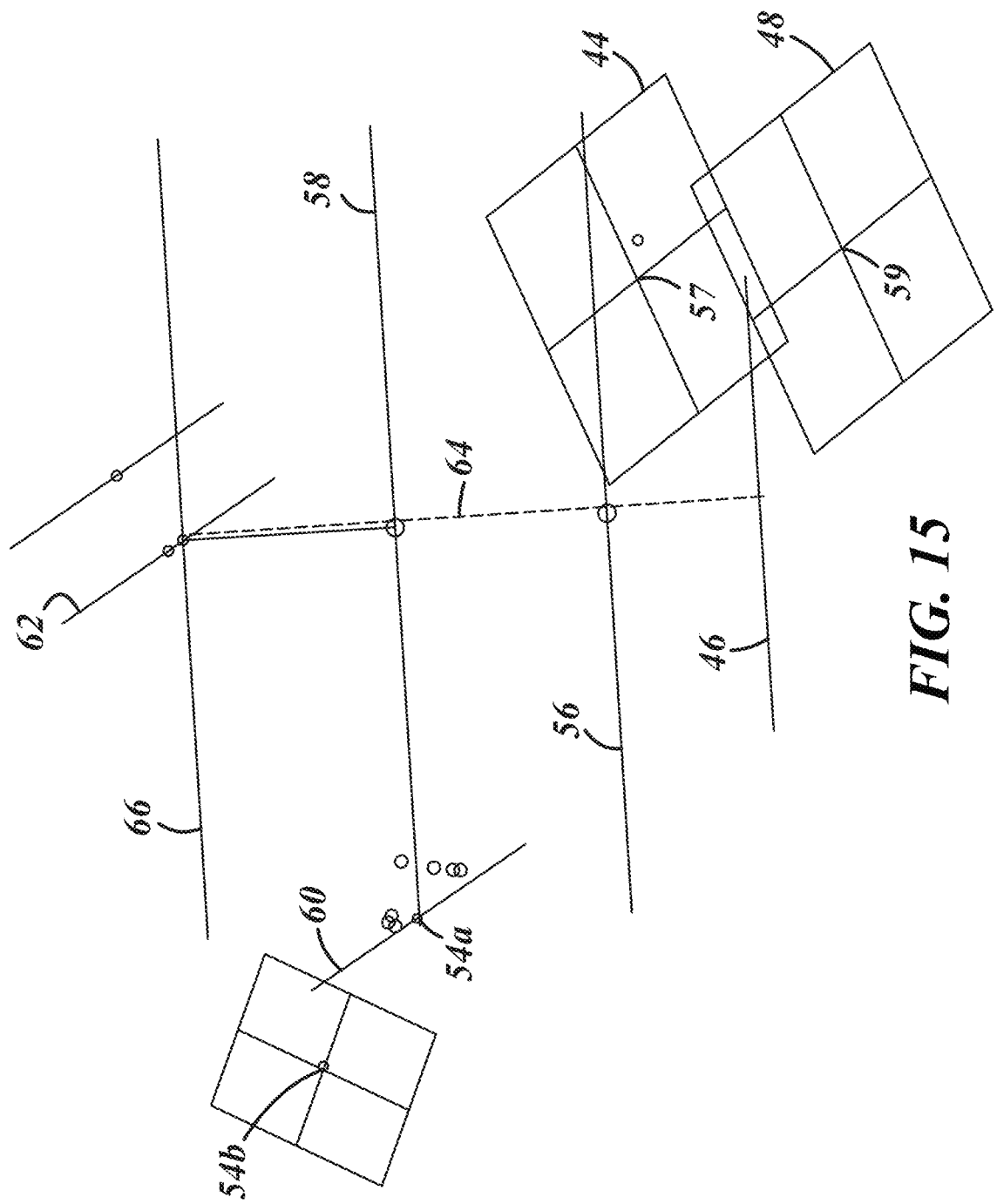
Figure 16:
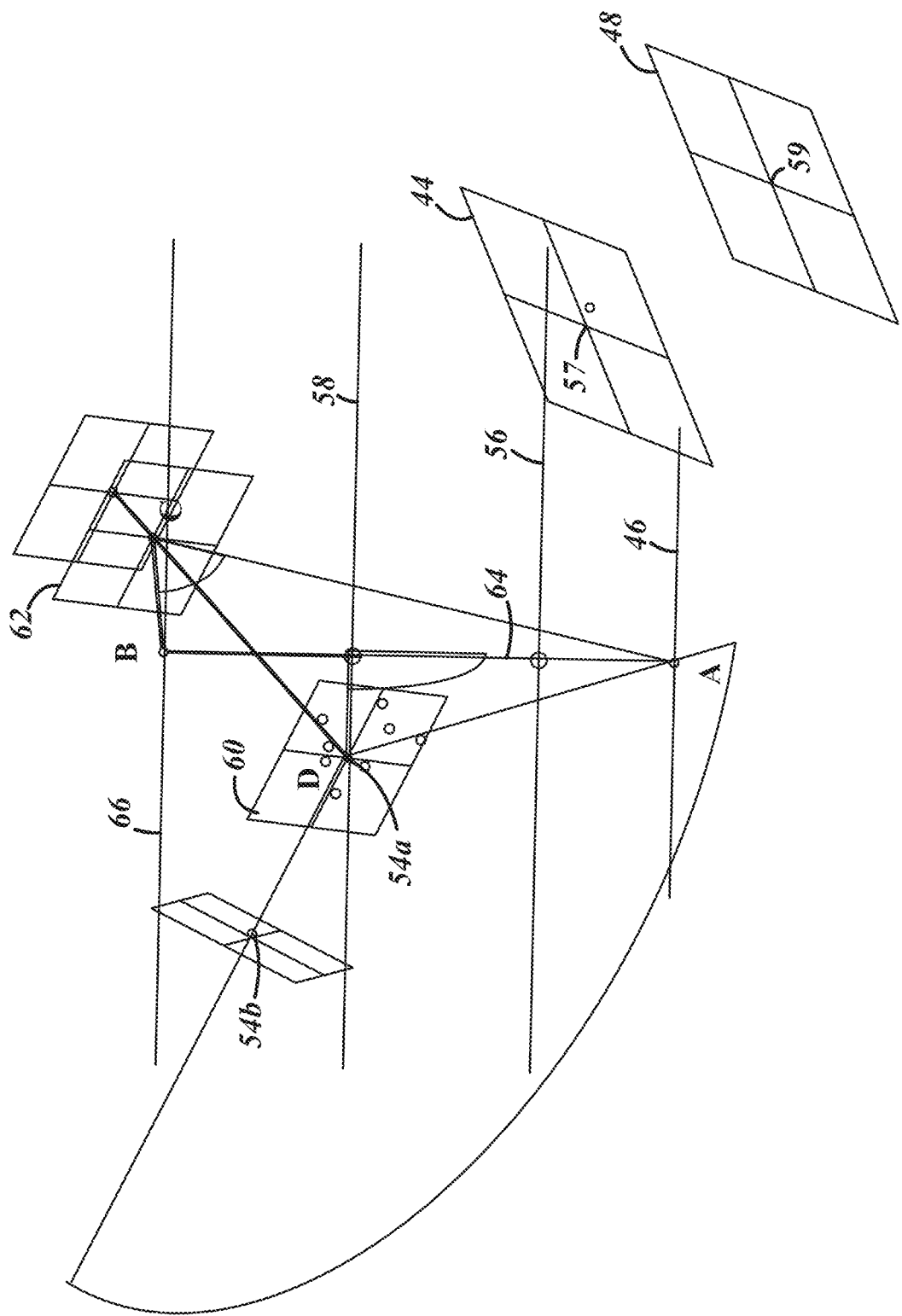

For example, and with reference to FIG. 15, in an embodiment wherein method 100 is used to select a medical device for use in a procedure relating to the mitral valve, method 100 may include a step (not shown) that is performed before step 120 and that comprises duplicating the plane represented in FIGS. 15 and 16 as reference numeral 60 that contains the origin/centroid 54a of the fossa ovalis (i.e., fossa ovalis plane), and moving or offsetting the duplicate plane or a representation of the plane 60 (represented as reference numeral 62 in FIGS. 15 and 16) along its origin until it intersects with an axis 64 of the origin of the mitral plane 46. The mitral plane 46 is then duplicated yet again, and the duplicated plane or representation of the plane 46 (represented by reference numeral 66 in FIGS. 15 and 16) is moved or offset to the point at which the offset fossa ovalis plane 62 intersects with the axis 64.

As shown in FIG. 15, in at least some embodiments, this step may be performed using a view wherein all mitral plane edges and the fossa ovalis plane edge are aligned. In any event, the step described above may be performed automatically by the ECU 28 of the system 26 (e.g., by the processor 34 of the ECU 28) using, for example, suitable image processing software/techniques. Alternatively, the step may be performed by a user (e.g., physician) manipulating the user interface device(s) 32 of the system 26. More specifically, the user may manipulate a computer mouse to cause the mitral plane 46 and fossa ovalis plane 60 displayed on the display 30 of the system 26 to be duplicated one or more times, and to then move (e.g., drag) the duplicate offset plane(s) to the desired point(s) or location(s). Additionally, it will be appreciated that in some embodiments wherein portions of the depiction acquired in step 106 may be hidden, structures that were previously hidden during the performance of other steps of method 100 may be displayed in order to facilitate the performance of this step.

In an embodiment wherein method 100 includes the step described above, step 120 comprises using the points identified in step 114, the planes defined in one or more steps 116, 118, and the intersection point(s) described above to determine or calculate various measurements. For example, and with reference to FIGS. 16 and 17, one or more of the following eight (8) different measurements may be determined and used to determine select a medical device.

A first measurement is the distance between the origin of the mitral plane 46 and the origin of the offset mitral plane 66 (i.e., the distance between points "A" and "B" in FIG. 16).

A second measurement is the distance between the origin of the mitral plane 46 and the intersection point of the offset mitral plane 66 and the offset fossa ovalis plane 62 (i.e., the distance between points "A" and "C" in FIG. 16).

A third measurement is the distance between the origin of the offset mitral plane 66 and the intersection point of the offset mitral plane 66 and the offset fossa ovalis plane 62 (i.e., the distance between points "B" and "C" in FIG. 16).

A fourth measurement is the angle formed by the points corresponding to the origin of the offset mitral plane 66, the origin of the mitral plane 46, and the intersection point of the offset mitral plane 66 and the offset fossa ovalis plane 62 (i.e., the angle "BAC" in FIG. 16).

A fifth measurement is the angle formed by the points corresponding to the origin of the mitral plane 46, the origin of the offset mitral plane 66, and the intersection point of the offset mitral plane 66 and the offset fossa ovalis plane 62 (i.e., the angle "ABC" in FIG. 16).

A sixth measurement is the angle formed by the points corresponding to the origin of the mitral plane 46, the intersection point of the offset mitral plane 66 and the offset fossa ovalis plane 62, and the origin of the offset mitral plane 66 (i.e., the angle "ACB" in FIG. 16).

A seventh measurement is the angle formed by the points corresponding to the origin/centroid 54*b* of the IVC ostium, the origin/centroid 54*a* of the fossa ovalis, and the origin of the mitral plane 46 (i.e., the angle at point "D" in FIG. 16).

Figure 17:
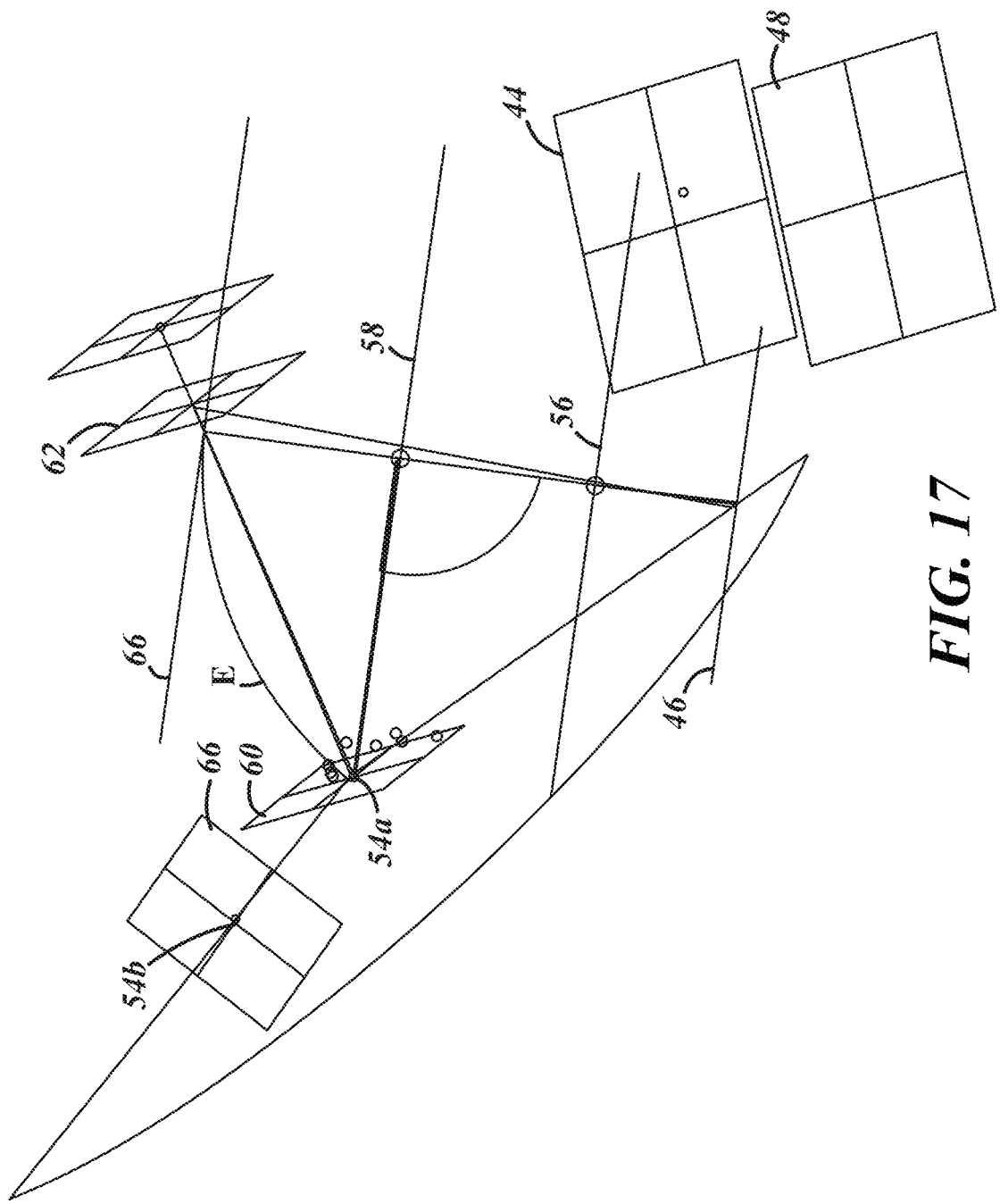

And an eighth measurement is the angle formed by the points corresponding to the origin/centroid 54*a* of the fossa ovalis, the origin of the mitral plane 46, and the origin of the offset mitral plane 66 (i.e., the angle "DAB" in FIG. 16 and shown as angle "E" in FIG. 17.)

Again, it will be appreciated that while certain specific measurements are identified and discussed above, in other embodiments, one or more measurements in addition to or instead of those described above may be determined. Additionally, as shown in FIGS. 14 and 15-17, in at least some embodiments, some or all of the depiction 40 acquired in step 106 may be hidden to provide a clear view of the measurements being determined in step 120.

Regardless of the particular measurement(s) determined in step 120, in an embodiment, step 120 may be performed automatically by the ECU 28 of the system 26 (e.g., by the processor 34 of the ECU 28) using, for example, suitable software/techniques. Alternatively, step 120 may be performed by a combination of the ECU 28 and user input. More particularly, a user (e.g., physician) may manipulate the user interface device 32 to select the measurement(s) to be determined (e.g., select two points between which a distance is to be determined, select three points that define the angle that is to be determined, etc.), and then the ECU 28 may determine/calculated the appropriate, selected measurement(s). Accordingly, the present disclosure is not intended to be limited to any particular way of performing step 120.

As illustrated in FIG. 3, once the appropriate measurement(s) is/are determined in step 120, method 100 proceeds to a step 122 of selecting or determining a medical device based on that or those measurements determined in step 120. In an embodiment, a data structure, for example, an empirically-derived look-up table (e.g., a multi-dimensional look-up table) that is configured to correlate the measurement(s) determined in step 120 (input(s)) with different types (e.g., sizes, shapes, etc.) of medical devices (output) is used to select/determine the appropriate medical device. In an embodiment, the data structure may be stored in a memory of the system 26 (e.g., the memory 36 of the ECU 28), and the processor 34 of the ECU 28 may be configured to look up the measurements determined in step 120 in the data structure to select or determine an appropriate medical device to use. It will be appreciated, however, that other suitable ways/technique for selecting a medical device may certainly be used instead.

In addition to the foregoing, in at least some embodiments, the appropriateness or suitability of one or more insertion points through an anatomical structure and/or one or more medical devices used to perform the medical procedure may be evaluated. In an embodiment, this evaluation may comprise part of the method 100, and thus, the steps of the evaluation process may be performed after one or more of the above-described steps of method 100 (e.g., after one or more of steps 106-122). It will be appreciated, however, that the steps of the evaluation process may also be performed independently of method 100, or may require only some of the steps of method 100. For purposes of illustration only, the description below will be with respect to insertion points through the interatrial septum, and the fossa ovalis in particular, and medical devices comprising catheters (e.g., catheters used in procedures relating to the implantation of LAA occlusion devices). It will be appreciated, however, that the appropriateness of insertion points through other anatomical structures and/or devices other than catheters may be evaluated in the manner described below.

Figure 18:
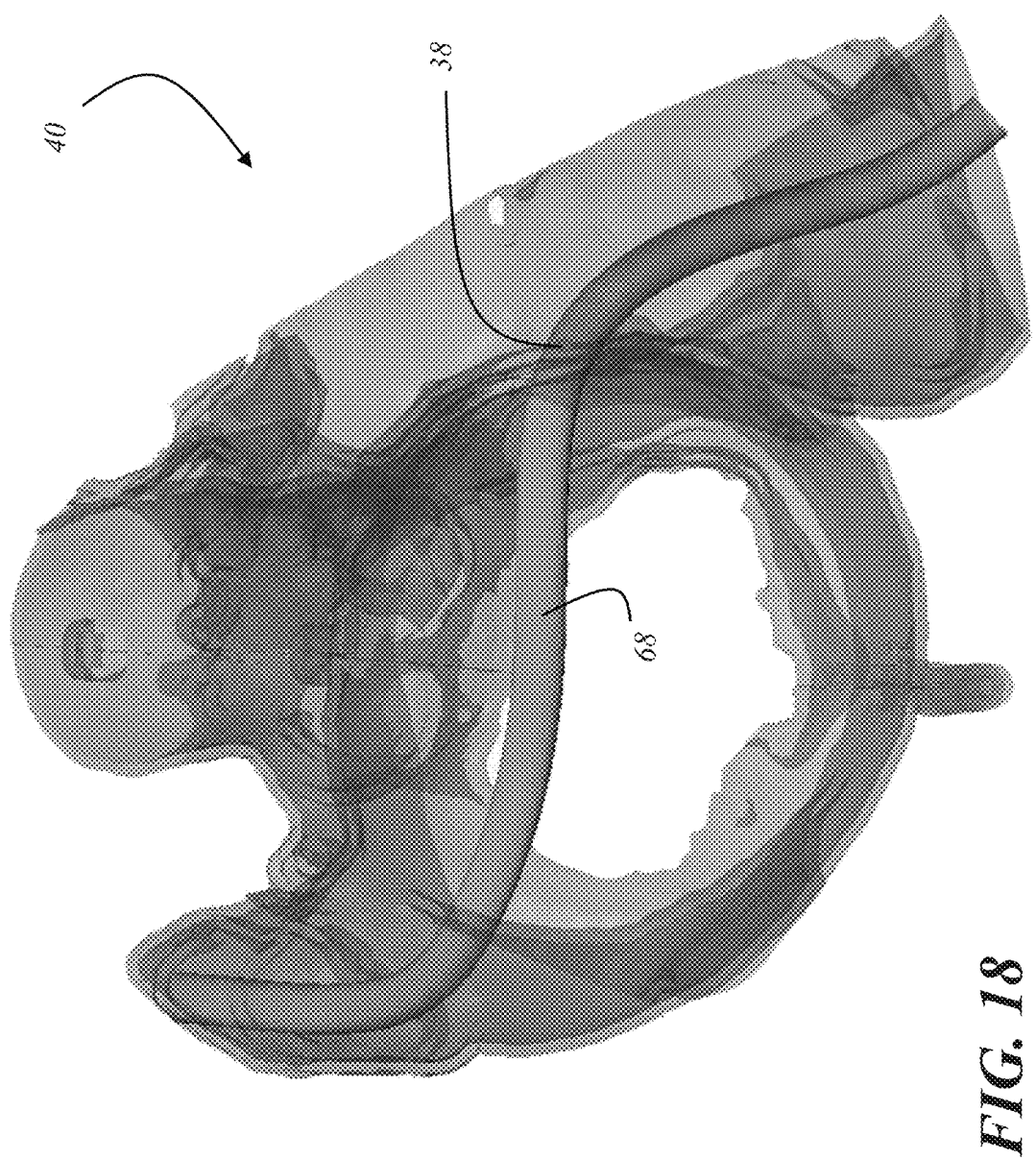
FIG. 18 shows a depiction of an anatomical structure having a model of a medical device imported therein for use in performing one or more steps a method used to evaluate the appropriateness of, for example, the medical device.

In at least some embodiments, the evaluation process includes a step of identifying or one or more insertion points through the interatrial septum. The depiction 40 acquired in step 106 or a different depiction acquired in a similar manner as that described in step 106 may be used to identify or select one or more possible insertion points. The possible insertion points may be identified or selected in any number of ways, including, for example and without limitation, in the manner described elsewhere above with respect to the identification of markers 38. FIG. 18 illustrates the depiction 40 having a single insertion point represented by marker 38; though it will be appreciated that more than one insertion point may certainly be identified.

Once one or more insertion points are identified, one or more models of one or more medical devices (e.g., catheters) may be selected and imported into the depiction 40. In an illustrative embodiment, the identified insertion points are evaluated individually one at a time, with one or more selected models being imported into the depiction for a given insertion point. In other embodiments, however, multiple insertion points may be evaluated at the same time, with one or more models being imported for each insertion point.

The selection of a model of a device may be carried out in a number of ways. In at least some embodiments, the selection of a model of a particular medical device may be made from a number of different models having different characteristics. For example, in an illustrative embodiment, a particular model may be selected from a series of models representative of devices from different manufactures, devices having different material properties assigned thereto, and/or devices having different shapes, sizes, geometries (e.g., lengths, diameters, curvatures (both number and degrees of curvature(s)), minimum/maximum bend radii, and/or other characteristics). The selection may also be from models of devices used for different procedures. Accordingly, it will be appreciated that the selection of a model (or models) may be based on a number of factors/characteristics, including, but not limited to, those identified above.

In an embodiment, the models from which a selection is made may be contained in a digital library or database that may be stored in or on a suitable component of the system 26, or a component that is accessible by system 26. In one illustrative embodiment, the library or database containing the models is stored in or on the memory device 36 of the ECU 28 of the system 26. The model selection may be made automatically by the system 26 (i.e., the processor 34) or may be made manually by a user via, for example, the user interface device(s) 32, the display devices 30, or a combination of the user interface device 32 and display 30. In the latter instance, a list of possible models may be displayed on the display device 30 and a user may manipulate the user interface device 32 (or the display device itself) to select the desired model(s). The models in the list may be identified by words describing the model and/or the device represented thereby (e.g., manufacture name, device name, device model number, etc.). Additionally, or alternatively, visual depictions of the models themselves may be displayed (e.g., thumbnail images of the models/devices).

In an illustrative embodiment, one or more user-inputtable or user-selectable fields (e.g., radio buttons, drop-down menus, text boxes for entering information, etc.) may be displayed to allow a user to provide certain information that the system 26 can use to narrow down the universe of models from which the selection is made. This may include, for example, the name of a preferred device manufacturer, the name of the procedure to be performed, etc. In response to the user input, the system 26 may automatically select the model(s) to be used, or may present a list of models from which a selection can be made by the user.

In view of the foregoing, it will be appreciated that the selection of one or more models of one or more medical devices may be carried out in a number of ways, including, but certainly not limited to, those described above.

In certain embodiments, the selection of a model results in the selected model being imported into the depiction 40, or at least displayed along with the depiction 40. In other embodiments, however, a user must affirmatively command the importation of a selected model by, for example, manipulating an "import" button that may be displayed or disposed on the display 30 or on the user interface 32. In an illustrative embodiment, an imported model is automatically placed and positioned within the depiction 40 in such a way that it shows how the device represented by the model would be disposed if actually used in the performance of the medical procedure (i.e., it shows the model in the landing position of the device). For example, in an instance wherein the medical procedure involves the implantation of an LAA occlusion device and the model is a model of a catheter used in the performance of such a procedure, the model of the catheter may be placed such that the distal tip of the catheter model is located proximate (i.e., near or in) the LAA ostium. The user may then be able to fine tune the position of the model using, for example, the user interface device 32 by translating and/or rotating the model. The system 26 may be configured to automatically position the model based on certain pre-defined points within or relative to the depiction 40, including, for example, an identified insertion point through the interatrial septum. These points may include some or all of the points defined in step 114 of method 100 described above. For example, in FIG. 18, the positioning of a model 68 within the depiction 40 is defined or dictated by a plurality of points defined in step 114, namely, the origin of a plane that contains the IVC ostium, the origin of a plane that contains the fossa ovalis, and the origin of a plane that contains the true ostium of the LAA. In other embodiments, the points used in the automatic placement/positioning of the model may comprise additional and/or different points than those defined in step 114 that is/are defined manually by the user or automatically by the system 26.

In other embodiments, rather than the model being automatically placed as described above, the user may be able to manually place the model at one or more desired locations using, for example, the user interface device 32. For example, the user may "click" and "drag" the model to a desired position within the depiction 40. Alternatively, the user may use "translate" and/or "rotate" tools to move the model to a desired location. In such am embodiment, the user may also reposition the model to a different desired location within the depiction 40.

Once one or more device models have been imported for one or more insertion points, the trajectory of each imported model for each respective insertion point can be viewed or determined, and a determination can be made as to the appropriateness of each device and/or the respective insertion point(s). More particularly, FIG. 18 shows the model 68 imported into the depiction 40 relative to an insertion point 38. The model 68 is placed such that it is positioned at a location corresponding to a desired landing point of the device represented by the model 68. The user may then view the trajectory that the device would have relative to various anatomical structures shown or represented in the depiction 40, and then determine, based at least in part and the trajectory, whether the device represented by the model 68, and/or the insertion point 38, is/are appropriate.

Additionally, or alternatively, the system 26, and the ECU 28 thereof in particular, may be configured to make the determination as to the appropriateness of the device and/or insertion point automatically. More specifically, information relating to the device represented by the model 68 (i.e., minimum bend radius, maximum diameter, etc.) may be stored in, for example, the memory device 36 or another suitable memory device that is part of or accessible by the system 26. The processor 34 of the ECU 28 of the system 26, or another suitable component of system 26 or otherwise, may be configured to access the device information and use it to grade or determine the appropriateness of the device and/or a given insertion point. The points defined in, for example, step 114 may also be used along with this information to determine the appropriateness of the device and/or a given insertion point.

If only the appropriateness of the device is being evaluated, and it is determined that the device is appropriate, then the user may select that device for use in performing the procedure. Otherwise, the above-described process may be repeated for a different device, or if multiple devices were being evaluated at the same time, the user may select a device deemed to be most appropriate. If only the appropriateness of the insertion point is being evaluated, and it is determined that the insertion point is appropriate, then the user may select that insertion point as the target insertion point for the procedure. Otherwise, the above-described process may be repeated for a different insertion point, or if multiple insertion points were being evaluated at the same time, the user may select the insertion point deemed to be most appropriate. Finally, if the appropriateness of the device and the insertion point are being evaluated, and it is determined that both a given insertion point and a given device are appropriate, then the user may select that device and insertion point for use in performing the procedure. Otherwise, the above-described process may be repeated for a different device/insertion point combination, or if either multiple devices and/or multiple insertion points were being evaluated at the same time, the user may select the device/insertion point combination deemed to be most appropriate.

Accordingly, it will be appreciated that the appropriateness or suitability of a medical device and/or insertion point through an anatomical structure may be determined in a variety of ways, including, but not limited to, those described above.

It is to be understood that the foregoing is a description of one or more embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "e.g.," "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A method for selecting a medical device for use in the performance of a medical procedure, comprising:
acquiring image data relating to an anatomical region of interest of a patient's body;
generating, with an electronic processor, a multi-dimensional depiction of the anatomical region of interest using the acquired image data, wherein the multi-dimensional depiction includes three dimensions;
defining a plurality of points relative to the multi-dimensional depiction, wherein at least two of the plurality of points correspond to a centroid of an anatomical structure of the patient's body, and wherein the plurality of points comprises two or more of the following individual points:
  a point within a mitral plane that contains a mitral annulus of the patient's heart, wherein the point corresponds to a centroid of the mitral annulus;
  a point within an offset mitral plane that is a duplicate of and offset from the mitral plane, wherein the point is offset from the point in the mitral plane and corresponds to the centroid of the mitral annulus;
  a point within a fossa ovalis plane that contains a fossa ovalis of the patient's heart, wherein the point corresponds to a centroid of the fossa ovalis; and
  a point within an inferior vena cava ("IVC") ostium plane that contains an IVC ostium of the patient's heart, wherein the point corresponds to a centroid of the ostium of the IVC;
determining, with the electronic processor, one or more measurements based on the defined plurality of points, wherein the measurement(s) determined in the determining step comprise(s) at least one of:
  an angle formed by the point within the IVC ostium plane corresponding to the centroid of the ostium of the IVC, the point within the fossa ovalis plane corresponding to the centroid of the fossa ovalis, and the point in the mitral plane corresponding to the centroid of the mitral annulus, wherein the point within the fossa ovalis plane corresponding to the centroid of the fossa ovalis is the vertex of the angle; or
  an angle formed by the point within the fossa ovalis plane corresponding to the centroid of the fossa ovalis, the point within the mitral plane corresponding to the centroid of the mitral annulus, and the point within the offset mitral plane corresponding to the centroid of the mitral annulus, wherein the point within the mitral plane corresponding to the centroid of the mitral annulus is the vertex of the angle, and
selecting a medical device over another medical device based on the determined measurements, wherein the medical device is configured to fit into an insertion point of interest.

2. The method of claim 1, further comprising:
identifying in the depiction the insertion point along an interatrial septum;
selecting a model representative of the medical device that will pass through the interatrial septum during the performance of the medical procedure;
importing the model of the medical device into the depiction, wherein the model is positioned within the depiction relative to the identified insertion point; and
evaluating feasibility of the insertion point, a type, shape, and/or size of the medical device, or both the feasibility of the insertion point and the type, shape, and/or size of the medical device based on a trajectory of the model of the medical device within the depiction.

3. The method of claim 1, further comprising receiving at least one user input, and in response to that at least one user input, the method further comprising:
identifying in the depiction the insertion point along an interatrial septum;
selecting a model representative of the medical device that will pass through the interatrial septum during the performance of the medical procedure;
importing the model of the medical device into the depiction, wherein the model is positioned within the depiction relative to the identified insertion point.

4. The method of claim 1, wherein the measurement(s) determined in the determining step further comprise:
a distance between the point within the mitral plane corresponding to the centroid of the mitral annulus and the point within the offset mitral plane corresponding to the centroid of the mitral annulus.

5. The method of claim 1, wherein the measurement(s) determined in the determining step comprise(s) at least one of:
a distance between an origin of the mitral plane and an intersection point of the offset mitral plane and an offset fossa ovalis plane;
a distance between an origin of the offset mitral plane and the intersection point of the offset mitral plane and the offset fossa ovalis plane; or
an angle containing the origin of the mitral plane, the origin of the offset mitral plane, and the intersection point of the offset mitral plane and the offset fossa ovalis plane.

6. A non-transitory, computer-readable storage medium storing instructions thereon that when executed by an electronic processor causes the electronic processor to carry out the method of:
acquiring image data relating to an anatomical region of interest of a patient's body;
generating a multi-dimensional depiction of the anatomical region of interest using the acquired image data, wherein the multi-dimensional depiction includes three dimensions;
defining a plurality of points relative to the multi-dimensional depiction, wherein at least two of the plurality of points correspond to a centroid of an anatomical structure of the patient's body, and wherein the plurality of points comprises two or more of the following individual points:
  a point within a mitral plane that contains a mitral annulus of the patient's heart, wherein the point corresponds to a centroid of the mitral annulus;
  a point within an offset mitral plane that is a duplicate of and offset from the mitral plane, wherein the point is offset from the point in the mitral plane and corresponds to the centroid of the mitral annulus;
  a point within a fossa ovalis plane that contains a fossa ovalis of the patient's heart, wherein the point corresponds to a centroid of the fossa ovalis; and a point within an inferior vena cava ("IVC") ostium plane that contains an IVC ostium of the patient's heart, wherein the point corresponds to a centroid of the ostium of the IVC;

determining, with the electronic processor, one or more measurements based on the defined plurality of points, wherein the measurement(s) determined in the determining step comprise(s) at least one of:

an angle formed by the point within the IVC ostium plane corresponding to the centroid of the ostium of the IVC, the point within the fossa ovalis plane corresponding to the centroid of the fossa ovalis, and the point in the mitral plane corresponding to the centroid of the mitral annulus, wherein the point within the fossa ovalis plane corresponding to the centroid of the fossa ovalis is the vertex of the angle; or an angle formed by the point within the fossa ovalis plane corresponding to the centroid of the fossa ovalis, the point within the mitral plane corresponding to the centroid of the mitral annulus, and the point within the offset mitral plane corresponding to the centroid of the mitral annulus, wherein the point within the mitral plane corresponding to the centroid of the mitral annulus is the vertex of the angle, and selecting a medical device over another medical device based on the determined measurements, wherein the medical device is configured to fit into an insertion point of interest.

7. The storage medium of claim 6, wherein the method carried out by the one or more processors further comprises:

identifying in the depiction the insertion point along an interatrial septum;

selecting a model representative of the medical device that will pass through the interatrial septum during the performance of the medical procedure;

importing the model of the medical device into the depiction, wherein the model is positioned within the depiction relative to the identified insertion point; and evaluating feasibility of the insertion point, a type, shape, and/or size of the medical device, or both the feasibility of the insertion point and the type, shape, and/or size of the medical device based on a trajectory of the model of the medical device within the depiction.

8. The storage medium of claim 6, wherein the method carried out by the one or more processors further comprises receiving at least one user input, and in response to that at least one user input, the method further comprises:

identifying in the depiction the insertion point along an interatrial septum;

selecting a model representative of the medical device that will pass through the interatrial septum during the performance of the medical procedure;

importing the model of the medical device into the depiction, wherein the model is positioned within the depiction relative to the identified insertion point.

9. The storage medium of claim 6, wherein the measurement(s) determined in the determining step further comprise:

a distance between the point within the mitral plane corresponding to the centroid of the mitral annulus and the point within the offset mitral plane corresponding to the centroid of the mitral annulus.

10. The storage medium of claim 6, wherein the measurement(s) determined in the determining step comprise(s) at least one of:

a distance between an origin of the mitral plane and an intersection point of the offset mitral plane and an offset fossa ovalis plane;

a distance between an origin of the offset mitral plane and the intersection point of the offset mitral plane and the offset fossa ovalis plane; or an angle containing the origin of the mitral plane, the origin of the offset mitral plane, and the intersection point of the offset mitral plane and the offset fossa ovalis plane.

11. A system for selecting a medical device of use in a medical procedure, comprising:

an electronic processor; and an electronic memory electrically coupled to the electronic processor and having instructions stored therein, wherein the processor is configured to access the memory and execute the instructions stored therein such that it is operable to:

acquire image data relating to an anatomical region of interest of a patient's body;

generate a multi-dimensional depiction of the anatomical region of interest using the acquired image data, wherein the multi-dimensional depiction includes three dimensions;

define a plurality of points relative to the multi-dimensional depiction, wherein at least two of the plurality of points correspond to a centroid of an anatomical structure of the patient's body, and wherein the plurality of points comprises two or more of the following individual points:

a point within a mitral plane that contains a mitral annulus of the patient's heart, wherein the point corresponds to a centroid of the mitral annulus;

a point within an offset mitral plane that is a duplicate of and offset from the mitral plane, wherein the point is offset from the point in the mitral plane and corresponds to the centroid of the mitral annulus;

a point within a fossa ovalis plane that contains a fossa ovalis of the patient's heart, wherein the point corresponds to a centroid of the fossa ovalis; and a point within an inferior vena cava ("IVC") ostium plane that contains an IVC ostium of the patient's heart, wherein the point corresponds to a centroid of the ostium of the IVC;

determine, with the electronic processor, one or more measurements based on the defined plurality of points, wherein the measurement(s) determined in the determining step comprise(s) at least one of:

an angle formed by the point within the IVC ostium plane corresponding to the centroid of the ostium of the IVC, the point within the fossa ovalis plane corresponding to the centroid of the fossa ovalis, and the point in the mitral plane corresponding to the centroid of the mitral annulus, wherein the point within the fossa ovalis plane corresponding to the centroid of the fossa ovalis is the vertex of the angle; or an angle formed by the point within the fossa ovalis plane corresponding to the centroid of the fossa ovalis, the point within the mitral plane corresponding to the centroid of the mitral annulus, and the point within the offset mitral plane corresponding to the centroid of the mitral annulus, wherein the point within the mitral plane corresponding to the centroid of the mitral annulus is the vertex of the angle, and select a medical device over another medical device based on the determined measurements, wherein the medical device is configured to fit into an insertion point of interest.

12. The system of claim 11, wherein the processor is further operable to:
   identify in the depiction the insertion point along an interatrial septum;
   select a model representative of the medical device that will pass through the interatrial septum during the performance of the medical procedure;
   import the model of the medical device into the depiction, wherein the model is positioned within the depiction relative to the identified insertion point; and
   evaluate feasibility of the insertion point, a type, shape, and/or size of the medical device, or both the feasibility of the insertion point and the type, shape, and/or size of the medical device based on a trajectory of the model of the medical device within the depiction.

13. The system of claim 11, wherein in response to one or more user inputs, the processor is further operable to:
   identify in the depiction the insertion point along an interatrial septum;
   select a model representative of the medical device that will pass through the interatrial septum during the performance of the medical procedure; and
   import the model of the medical device into the depiction, wherein the model is positioned within the depiction relative to the identified insertion point.

14. The system of claim 11, wherein the measurement(s) further comprises:
   a distance between the point within the mitral plane corresponding to the centroid of the mitral annulus and the point within the offset mitral plane corresponding to the centroid of the mitral annulus.

15. The system of claim 11, wherein the measurement(s) determined in the determining step comprise(s) at least one of:
   a distance between an origin of the mitral plane and an intersection point of the offset mitral plane and an offset fossa ovalis plane;
   a distance between an origin of the offset mitral plane and the intersection point of the offset mitral plane and the offset fossa ovalis plane; or
   an angle containing the origin of the mitral plane, the origin of the offset mitral plane, and the intersection point of the offset mitral plane and the offset fossa ovalis plane.

* * * * *